United States Patent
Klocke et al.

(10) Patent No.: US 7,913,371 B2
(45) Date of Patent: Mar. 29, 2011

(54) MEDICATION DEPOT FOR MEDICAL IMPLANTS

(75) Inventors: Bjoern Klocke, Zurich (CH); Tobias Diener, Erlangen (DE); Matthias Fringes, Ansbach (DE); Claus Harder, Uttenreuth (DE)

(73) Assignee: Biotronik VI Patent AG, Baar (CH)

( * ) Notice: Subject to any disclaimer, the term of this patent is extended or adjusted under 35 U.S.C. 154(b) by 50 days.

(21) Appl. No.: 12/177,041

(22) Filed: Jul. 21, 2008

(65) Prior Publication Data
US 2009/0024210 A1    Jan. 22, 2009

(30) Foreign Application Priority Data
Jul. 20, 2007   (DE) .................. 10 2007 034 041

(51) Int. Cl.
*B23P 11/02*  (2006.01)
*A61F 2/82*   (2006.01)
*A61F 9/00*   (2006.01)

(52) U.S. Cl. .................. 29/453; 623/1.42; 427/2.14

(58) Field of Classification Search .............. 29/453, 29/428, 460, 527.2, 326.5, 426.6, 426.5; 623/1.42, 1.15; 427/2.14
See application file for complete search history.

(56) References Cited

U.S. PATENT DOCUMENTS

| | | | | |
|---|---|---|---|---|
| 5,935,162 | A | * | 8/1999 | Dang .................... 623/1.15 |
| 5,968,083 | A | | 10/1999 | Ciciarelli et al. |
| 5,968,093 | A | * | 10/1999 | Kranz .................... 623/1.15 |
| 6,197,047 | B1 | | 3/2001 | Kranz |
| 6,293,966 | B1 | | 9/2001 | Frantzen |
| 6,896,695 | B2 | | 5/2005 | Mueller et al. |
| 6,942,681 | B2 | | 9/2005 | Johnson |
| 2006/0241742 | A1 | | 10/2006 | Harder et al. |

FOREIGN PATENT DOCUMENTS

| | | |
|---|---|---|
| DE | 102005039126 A1 | 2/2007 |
| DE | 102006038232 A1 | 2/2008 |
| EP | 0884985 | 12/1998 |
| EP | 1430854 A1 | 6/2004 |

OTHER PUBLICATIONS

Search Report for German Patent Application No. 10 2007 034 041.0; Apr. 10, 2008.

* cited by examiner

*Primary Examiner* — John C Hong
(74) *Attorney, Agent, or Firm* — Jason A. Bernstein; Barnes & Thornburg LLP

(57) ABSTRACT

A method for producing an agent depot for mechanical connection to a surface of an endovascular implantable body, comprising a) providing one or more polymers; b) providing one or more agents; and c) producing an agent depot from said polymers and said agents, the agent depot being mechanically connectable to the surface of the body using force action or adhesive.

14 Claims, 20 Drawing Sheets

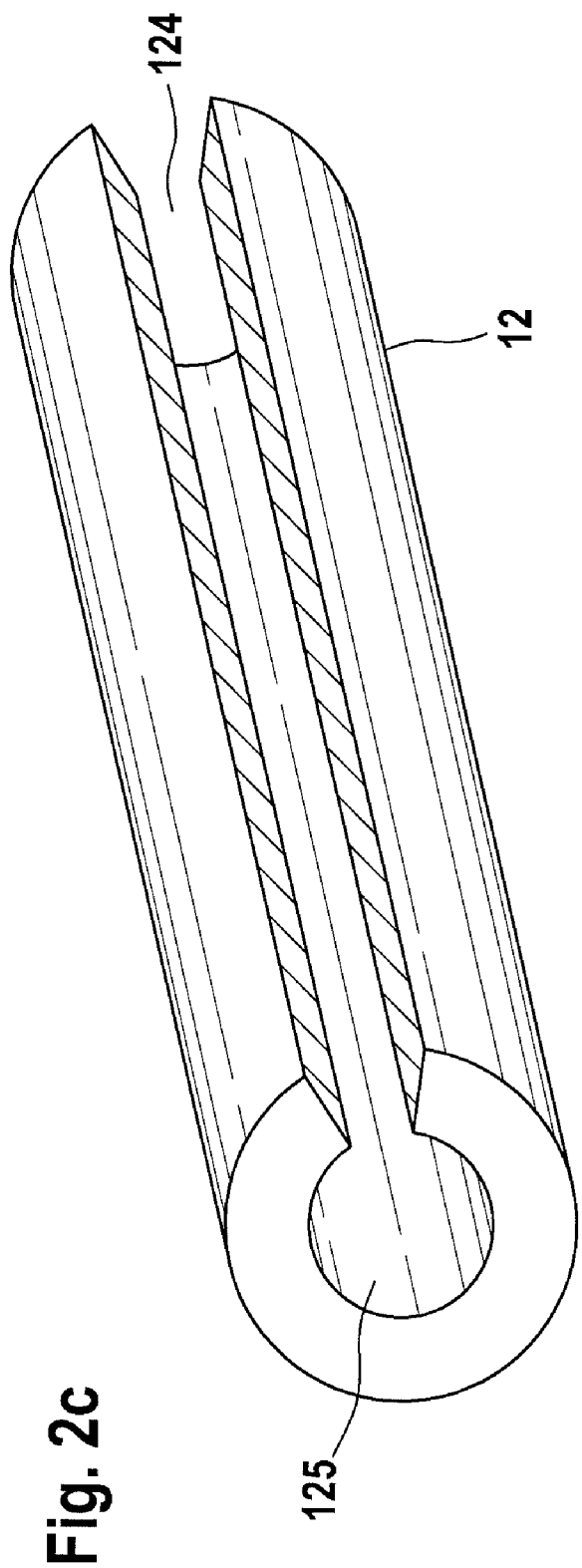

MEDICATION DEPOT FOR MEDICAL IMPLANTS

FIELD

The present disclosure relates to a method for producing an agent depot for an implantable body such as an endovascular stent; a method for producing an agent-coated endovascular implantable body; an agent-charged endovascular implantable body, producible according to the method; and, a kit comprising one or more agent depots, producible according to a method, and one or more endovascular implantable bodies.

BACKGROUND

Endovascular implantable bodies are used in medical technology, inter alia, for supporting vascular structures. In particular, endovascular prostheses and/or implants, in particular, endovascular stents, are used to treat coronary heart disease, in particular, acute myocardial infarction. Such bodies are also known for the treatment of aneurysms. Stents fundamentally have a support structure which is capable of supporting the wall of a vessel and widening the vessel and/or bypassing an aneurysm.

For this purpose, stents are inserted in a compressed state into the vessel and then expanded at the location to be treated and pressed against the vascular wall. This expansion may be performed with the aid of a balloon catheter, for example. Alternatively, self-expanding stents are also known. These are constructed from a superelastic metal, such as Nitinol.

However, extremely small injuries and cracks (dissections) arise in the vascular wall with the expansion of the blood vessel, which frequently heal without problems, but may result in approximately one-third of the cases in growths (proliferation) and finally in renewed vascular constriction (restenosis) due to the triggered cell growth. The expansion of the vessel by endovascular stents additionally does not remove the causes of the original stenosis, i.e., the molecular pathological changes in the vascular wall. One cause of restenosis is also the excess elasticity of the blood vessels stretched by the stent. The stretched blood vessel typically constricts excessively after removal of the balloon, so that the vascular cross-section is decreased in relation to the area of the blood vessel which was not stretched (obstruction, so-called negative remodeling). The latter effect may be avoided by the placement of an endovascular implant, typically a stent.

The introduction of stents into interventional treatment of stable and unstable angina pectoris in coronary heart diseases has resulted in a significant reduction of the rate of restenosis and thus in better long-term results, which is primarily to be attributed to the lumen acquisition, however, the extremely small injuries which occur, which may induce the proliferation, may in turn trigger a restenosis. In addition, the presence of a foreign body of this type in the vascular system may initiate a cascade of cellular molecular processes, which may result in a gradual overgrowth of the vessel (in particular also thrombosis) in the area in which the implant, in particular the stent, is implanted.

For some years, attempts have therefore been made to reduce the danger of restenosis upon the implantation of stents further by using stents coated with agents (local drug delivery (LDD); drug eluting stents (DES)). However, agent carriers which are implanted in vessels are also used in illnesses which are not coronary-related (drug reservoirs for non-coronary applications (cancer treatment, etc.)).

The carriers of agent-containing coating systems of this type typically consist of a biocompatible material which is either of natural origin or may be obtained synthetically. Numerous methods have been developed for applying the coating systems to the stent, such as rotation pulverization methods, immersion methods, and spraying methods. The coating system at least regionally covers the surface of the stent, a release of the pharmacological agent into the human or animal body occurring through gradual degradation of the carrier and/or diffusion into the surrounding tissue.

An agent-containing coating of endovascular stents is typically to be understood as a flat coating. However, the coatings may also partially comprise the existing holes and/or cavities of the stent geometry being filled or single-sided or punctual coatings existing on the support structure of the stent. Such coatings are, however, very technologically demanding and also time-consuming and costly. It has now been established that not all coating materials may be coated with and without incorporated agent(s) directly on the implantable body according to the typically used methods.

In general, in most coating methods prior dissolving of the polymer matrix is necessary before the coating. However, to ensure the necessary freedom from solvent of the "drug eluting" implant, sometimes complex method steps must be performed to extract the same solvent, which are performed after the coating step.

Because of differing physical-chemical properties of substrate surface and coating material (hydrophobic, hydrophilic properties), the desired surface properties of the implant to be produced may possibly not be achieved. To still achieve these properties, though, sometimes complex method steps are required for pretreating the particular surface, which may possibly also have consequences for the biocompatibility because of an additional manufacturing step.

Agent-charged polymer layers having a high agent charge may also in particular result in mechanical problems of the layer upon the dilation of the stent.

In the known coating forms of stents, one is typically restricted to one agent-dose combination, because it is very difficult to implement coatings which have different elution rates of an agent or elutions of multiple agents (multiple drug release, in particular dual-drug release, triple-drug release, etc.), in particular at different elution rates.

SUMMARY

The present disclosure describes several exemplary embodiments of the present invention.

One aspect of the present disclosure provides a method for producing an agent depot for mechanical connection to a surface of an endovascular implantable body, comprising a) providing one or more polymers; b) providing one or more agents; and c) producing an agent depot from said polymers and said agents, the agent depot being mechanically connectable to the surface of the body using either force action or adhesive.

Another aspect of the present disclosure provides a method for producing an agent-charged endovascular implantable body, comprising the steps of a) providing an endovascular implantable body; b) providing one or more different agent depots which are produced by (i) providing one or more polymers; (ii) providing one or more agents; and (iii) producing an agent depot from the polymers and the agents, the agent depot is mechanically connectable to the surface of the body using either force action or adhesive; and c) mechanically connecting one of said agent depots to said body.

A further aspect of the present disclosure provides an agent-charged, endovascular implantable body, said body produced according to a method, comprising a) providing an endovascular implantable body; b) providing one or more different agent depots produced by (i) providing one or more polymers, (ii) providing one or more agents, and (iii) producing an agent depot from the polymers and the agents, the agent depot is mechanically connectable to the surface of the body using either force action or adhesive; and c) mechanically connecting one of said agent depots to said body.

An additional aspect of the present disclosure provides a kit, comprising a) one or more agent depots, said agent depots produced by providing one or more polymers, providing one or more agents, and producing an agent depot from the polymers and the agents, the agent depot being implemented in such a manner that the agent depot is mechanically connectable to the surface of the body using either force action or adhesive; and b) one or more endovascular implantable bodies.

Another aspect of the present disclosure provides a method for producing an agent-charged, endovascular implantable body for prophylaxis or treatment of a stenosis, an aneurysm, or a tumor tissue in a human or animal body, the agent depots being produced by providing one or more polymers, providing one or more agents, and producing an agent depot from the polymers and the agents, the agent depot being implemented in such a manner that the agent depot is mechanically connectable to the surface of the body using either force action or adhesive.

Yet another aspect of the present disclosure provides a method for prophylaxis or treatment of a stenosis, an aneurysm, or a tumor tissue of a human or animal body, comprising a) providing an endovascular implantable body; b) providing one or more different agent depots, said agent depots produced by providing one or more polymers; providing one or more agents; and producing an agent depot from the polymers and the agents, the agent depot being implemented in such a manner that the agent depot is mechanically connectable to the surface of the body using either force action or adhesive; c) mechanically connecting one of said agent depots to said body; and d) implanting the agent-charged body produced in step c) in a blood vessel which carries blood to the tumor tissue.

One feature of the present disclosure provides an agent depot which may be bound to an endovascular implantable body, independently of its material. A further feature of the present disclosure provides an endovascular implantable body which comprises one or more agent depots having one or more agents, the agents being adjustably targeted to the elution time and concentration. A further feature addresses reduction of undesired implant side effects, e.g., increase of the restenosis and/or thrombosis risk.

The present invention is based on the finding that an agent depot according to the present disclosure, which may be manufactured separately from the actual endovascular implantable body, may be optimized in a technologically simpler manner in regard to the elution characteristic of the incorporated agents on one hand and may be directly mechanically connected to the implantable body, preferably the stent, independently of the material used on the other hand. Therefore, the agent depots produced according to the present disclosure, are mechanically connected to the endovascular implantable body, preferably in a form-fitting manner Accordingly, advantages of an implantable body produced according to the present disclosure having agent depots according to the present disclosure are particularly that as a result of the technological separation of the production of the implantable body and of the agent depot, a direct agent charge of the implantable body is made possible independently of the material of the implantable body.

A further feature is that a charge of an implantable body produced according to the present disclosure with one or more agent depots according to the present disclosure allows a flexible agent therapy of the implantable body custom tailored for the particular illness. A charge of an implant with one or more agent depots according to the present disclosure is technologically simple and already existing endovascular implantable bodies, whether or not they are agent-coated, may also be charged using the agent depots according to the present disclosure. In particular, different numbers of agent depots may also be charged in different spatial areas of the endovascular implantable body, preferably the stent. Exemplary embodiments are shown in FIGS. 2a and 2b. Such exemplary embodiments may be advantageous, in particular, if an individual agent treatment custom-tailored to a patient is necessary. In this case, the attending physician may perform the custom-tailored charging of an endovascular implantable body, preferably a stent, himself.

A further feature of the present disclosure is that not only one, but rather also multiple agents may be provided in the agent depot, in particular, in different doses, which, because of the limitation due to the layer thickness, may not be achieved using typical coatings of implantable bodies.

In particular, chronologically graduated elution curves of one or more agents may be implemented in the agent depot, for example, a continuous increase of one or more agents to accustom the body in which the implant having the agent depot is implanted to the agents step by step.

In typical agent-coated stents, charges of greater than 70% agent result in poor mechanical properties, in particular, in breaking off of the agent layer as well as often very short elution kinetics which are not always desirable.

Because of the typical layer thicknesses of 50 to 100 µm, stent geometries may arise which occupy an amount of volume of the vascular lumen which may result in problems during the implantation of the stent (deliverability) upon passage of stenoses or other constrictions (large "crossing profile").

In contrast to the typical coating methods, the use of agent depots according to the present disclosure, which are preferably clipped onto a body to be implanted, preferably a stent, allows the exploitation of the space between the struts and/or webs of the stent to be implanted or the clipping of the agent depot on the end of the body to be implanted, in particular, the stent. Especially with terminal clipping, agent depots which may comprise a high concentration of one or more agents may be used.

High agent concentrations are particularly advantageous for agents from the group consisting of limus agents for treating restenosis, in particular, comprising sirolimus (rapamycin), zotarolimus (Abt-578), tacrolimus (Fk506), everolimus, biolimus, in particular, biolimus A9, paclitaxel (taxol), pimecrolimus, lipid regulators, preferably fibrates, immunosuppressants, vasodilatators, preferably sartane, calcium channel blockers, calcineurin inhibitors, preferably tacrolimus, antiphlogistics, preferably cortisone and diclofenac, anti-inflammatory agents, preferably imidazole, antiallergens, oligonucleotides, preferably decoy oligodeoxynucleotide (dODN), estrogens, preferably genistein, endothelial producers, preferably fibrin, steroids, proteins/peptides, proliferation inhibitors, analgesics, antirheumatic agents, and the like.

Higher agent concentrations may also be desirable for local cancer treatments, so that the agents from the group of cytostatics, if the implant is placed in a vessel supplying the tumor tissue, preferably in proximity to the tumor tissue, may be released directly into the blood vessel there and may be supplied at high concentration directly using the bloodstream to the tumor tissue. The possibility exists that side effects which are associated with the cytostatics used may be reduced.

Exemplary embodiments according to the present disclosure for the preferred features described above are shown as examples in FIGS. 3a and 5a.

A further feature of the present disclosure is that multiple agent depots which each comprise different agents may be connected to one endovascular implantable body and thus a multiple drug release (release of multiple agents), in particular, a dual-drug release (release of two agents) or a triple-drug release (release of three agents) may be achieved which may hardly be achieved technologically or may only be achieved at increased cost and/or time consumption by a typical coating method. An example of such a design according to the present disclosure is described in FIG. 2a.

A further feature of the present disclosure is that interactions between the agents used and the material used for the implantable body, preferably a stent, may be reduced. This is implemented, in particular, in that the endovascular implantable body, preferably a stent, is produced separately from the agent depot according to the present disclosure. This is useful, in particular, if degradable (main) bodies are employed, such as degradable stents, in particular, degradable metal stents, because a direct agent coating with the (main) body is possible only with difficulty or sometimes not at all using typical methods due to the interaction with the material of the body. The terminal linkage of one or more agent depots on degradable main bodies is more preferable because the distance between the mutually influencing materials is increased and thus the mutual influence may be reduced.

The preferred designs of the features according to the present disclosure are described hereinafter and in the claims and may also be understood from the description of the figures and the associated figures. The preferred designs relate to all features of the present disclosure even if no express reference thereto is disclosed.

BRIEF DESCRIPTION OF THE DRAWINGS

Various aspects of the present disclosure are described hereinbelow with reference to the accompanying figures. The figures show exemplary details of the abluminal surface of stent geometries of a stent main body and/or the agent depot according to the present disclosure in a perspective view or in cross-section. However, the present disclosure is not restricted to the stent geometries shown here and/or to the configuration of the agent depot shown.

FIG. 2c is a perspective view of a slotted agent depot in sleeve form 12;

Figure 1A:
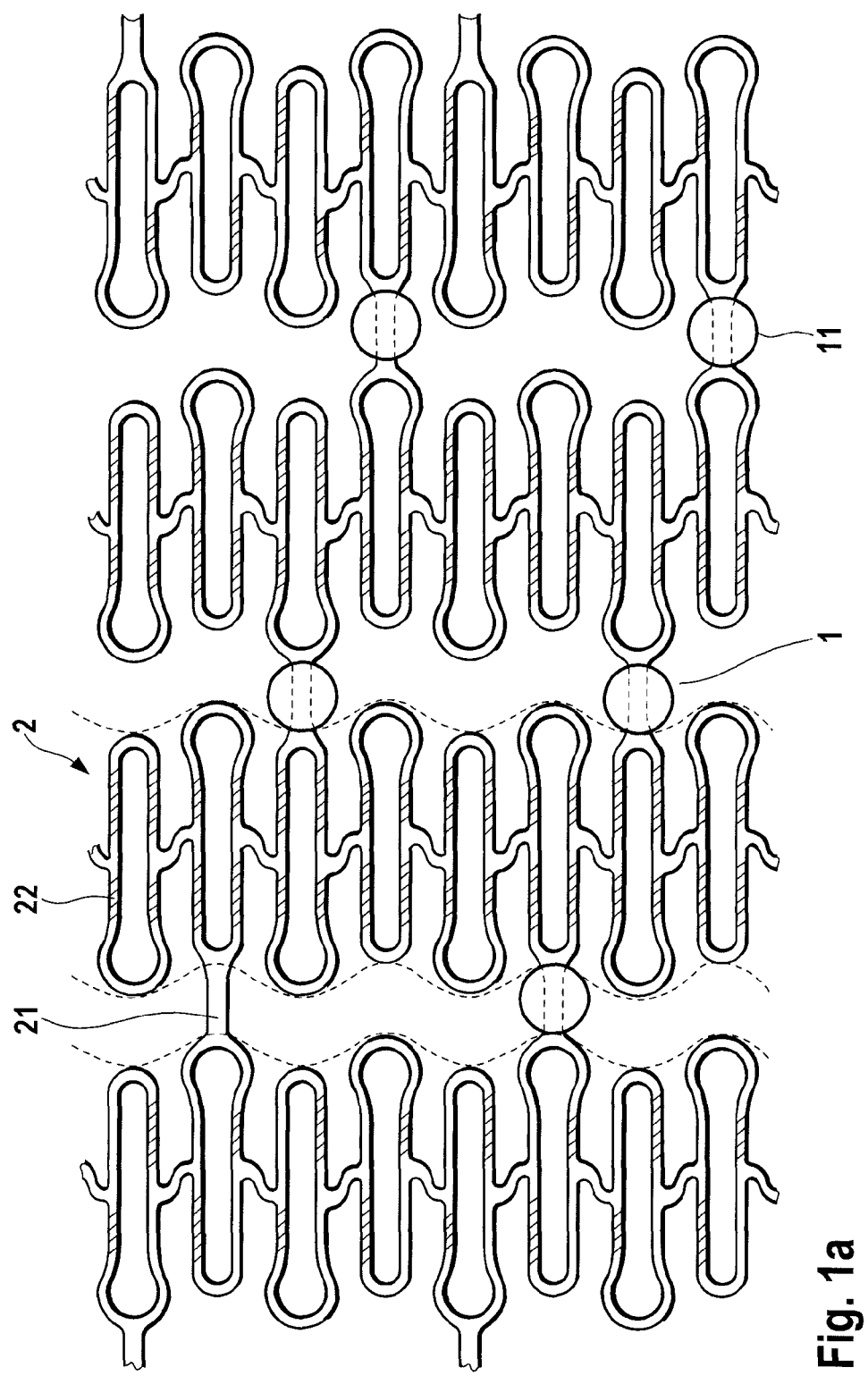
FIG. 1a is a top view of an abluminal detail of a stent geometry 2 having multiple agent depots 1 in bead form 11.

For purposes of the present disclosure, an implantable body typically represents, on one hand, a degradable or non-degradable, cardiovascular or peripheral stent as well as a stent for other cavities, such as the esophagus, the gall duct, the urethra, the prostate, or the trachea. On the other hand, implantable bodies, for purposes of the present disclosure, may represent local drug delivery implants which are implanted endovascularly in the blood vessels or other cavities. Furthermore, implantable bodies may represent neuroapplications as well as subcutaneous applications for continuous agent release (such as hormone preparations), as well as stimulation electrons or regional drug delivery applications.

For purposes of the present disclosure, degradable bodies, preferably stents, comprise degradable metal or degradable polymer as materials.

Degradable Metal Material:

The degradable metallic material is preferably a biocorrodible alloy, selected from the group consisting of magnesium, iron, zinc, and tungsten; in particular, the degradable metallic material is a magnesium alloy.

The alloy, in particular, comprising magnesium, iron, zinc, and/or tungsten, is to be selected in composition so that the alloy is biocorrodible. For purposes of the present disclosure, alloys are considered to be biocorrodible when degradation occurs in physiological surroundings which finally results in the entire stent or the part of the stent formed from the material losing its mechanical integrity. For purposes of the present disclosure, an alloy is a metallic structure whose main component is magnesium, iron, zinc, or tungsten. For purposes of the present disclosure, the main component is the alloy component whose weight proportion in the alloy is highest. A proportion of the main component is preferably more than 50 wt.-%, more preferably more than 70 wt.-%.

If the material is a magnesium alloy, the material preferably contains yttrium and rare earth metals because an alloy of this type is distinguished due to its physiochemical properties and high biocompatibility, in particular, also its degradation products.

Alloys of the WE series (WE43, and the like) as well as magnesium alloys of the composition rare earth metals 5.2 to 9.9 wt.-%, thereof yttrium 0.0 to 5.5 wt.-%, and the remainder comprising zircon less than 1 wt.-% are especially preferable, magnesium making up the proportion of the alloy to 100 wt.-%. These magnesium alloys have already confirmed their special suitability experimentally and in initial clinical trials, i.e., the magnesium alloys display a high biocompatibility, favorable processing properties, good mechanical characteristics, and corrosion behavior adequate for the intended uses. For purposes of the present disclosure, the collective term "rare earth metals" includes scandium (21), yttrium (39), lanthanum (57) and the 14 elements following lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70) und lutetium (71).

In particular, if agent depots according to the present disclosure are connected to magnesium stents, undesired interactions of the acid-degradable polymer agent depot and the basic-degrading magnesium stent, in particular, the acceleration of the magnesium corrosion and thus a more rapid loss of the stent collapsing pressure resulting therefrom, may be reduced because of the spatial distance. The degradation of the polymer in the agent depot may also be slowed by the increased spatial distance, because of which less irritation of the tissue occurs and the polymer layer does not peel off of the implanted stent.

Degradable Polymer Body:

Bodies, particularly stents made of degradable polymers, preferably comprise polydioxanone; polyglycolide; polycaprolactone; polylactides, preferably poly-L-lactide, poly-D, L-lactide, and polymers and blends thereof, such as poly(L-lactide-co-glycolide), poly(D,L-lactide-co-glycolide), poly(L-lactide-co-D,L-lactide), poly(L-lactide-co-trimethylene carbonate), and triblock copolymers; polysaccharides, preferably chitosan, levan, hyaluronic acid, heparin, dextran, and cellulose; polyhydroxyvalerate; ethylvinylacetate; polyethylene oxide; polyphosphorylcholine; fibrin; albumin, and the like.

If endovascular implantable stents are used as the implantable bodies for purposes of the present disclosure, all typical stent geometries may be used. Stent geometries which are described in U.S. Pat. No. 6,896,695; U.S. Patent Publication No. 2006/241742; U.S. Pat. No. 5,968,083; European Patent Application No. 1 430 854; U.S. Pat. No. 6,197,047; and European Patent Application No. 0 884 985 are particularly preferred.

If stents are used as the endovascular implantable bodies, the agent depots are preferably mechanically connected to the stent after the stent is crimped on a catheter to be used. This sequence has the advantage that the agent depots are not impaired in their matrix by the procedure of crimping.

The mechanical connection of the agent depot produced according to the present disclosure to the endovascular implantable body, preferably an endovascular stent, may preferably be designed as form-fitting with a web or strut of the stent. Preferably using a C-shaped gripper, which preferably clips the agent depot to the implantable body, preferably a stent, in a form-fitting manner. Such a design according to the present disclosure is shown, for example, in FIGS. 1b, 2c, 3b, 4c, 4e, 5b, and 5c. However, all other fastening measures of the stent according to the present disclosure which one skilled in the art considers because of his experience in the art are hereby also claimed. These include, in particular, embodiments in hook form, which are shown as examples in FIG. 4b. Suitable agent depots may also be shrunk onto the endovascular implantable body, preferably stent, or parts thereof, as shown in FIGS. 6a and 6b.

Agent depots according to the present disclosure may also be glued onto an implantable body, preferably a stent, as shown in, for example, in FIGS. 7a-7d. According to the present disclosure, suitable agent depots preferably have concave points which cling to the struts of an implantable stent. Instant adhesives from the group consisting of acrylates, fibrin adhesives, fats, and polysaccharides are preferably suitable as the adhesive.

Agent depots which completely enclose a strut of a stent and are suitably connected to one another such that the agent depot may not unroll from the strut are also conceivable (see FIGS. 8a through 8e).

One or more agent depots, which possibly differ in the agent concentration and/or in the type of agent, may be clipped on each implantable body, preferably a stent. The agent depots are typically designed so that they interfere in a vascular system as little as possible upon implantation of the body and are, therefore, housed in existing intermediate spaces of the implantable body, preferably a stent, or are pulled over the body, preferably a stent, as thin, compact sleeves. In a further exemplary embodiment, only the abluminal surface of an agent-charged body according to the present disclosure, preferably a stent, has the agent depot, in particular, the component of the agent depot which is coated with agent.

The polymers of the agent depot preferably include: non-degradable polymers: polyethylene; polyvinylchloride; polyacrylates; preferably polyethyl- and polymethylacrylates, polymethylmethacrylate, polymethyl-co-ethyl-acrylate, and ethylene/ethylacrylate; polytetrafluoroethylene, preferably ethylene/chlorotrifluoroethylene copolymers, ethylene/tetrafluoroethylene copolymers; polyamides, preferably polyamide imide, PA-11, PA-12, PA-46, PA-66; polyetherimide; polyethersulfone; poly(iso)butylene; polyvinylchloride; polyvinylfluoride; polyvinylalcohol; polyurethane; polybutylene terephthalate; silicones; polyphosphazene; polymer foams, preferably polymer foams made of carbonates, styrenes; copolymers and/or blends of the above-listed polymer classes, polymers of the class of thermoplastics, and degradable polymers: polydioxanone; polyglycolide; polycaprolactone; polylactides, preferably poly-L-lactide, poly-D,L-lactide, and copolymers and blends thereof, preferably poly(L- lactide-co-glycolide), poly(D,L-lactide-co-glycolide), poly (L-lactide-co-D,L-lactide), poly(L-lactide-co-trimethylene carbonate); triblock copolymers; polysaccharides, preferably chitosan, levan, hyaluronic acid, heparin, dextran, cellulose; polyhydroxyvalerate; ethylvinylacetate; polyethylene oxide; polyphosphorylcholine; fibrin; albumin; polyhydroxy butyric acid, preferably atactic, isotactic, and/or syndiotactic polyhydroxy butyric acid and their blends.

An agent depot produced according to the present disclosure is preferably produced in sleeve form (see FIGS. 2c and 4c, for example), film form (see FIG. 5b, for example), preform (see FIGS. 1b, 3b, 4b, 4e, and 5c, for example), or as a relatively rigid net. For purposes of the present disclosure, the term "sleeve" refers to a possibly flexible molded body which is round or oval in cross-section and is open on two sides. For purposes of the present disclosure, the term "preform" describes a negative shape of a point of the implant to which it is later attached. This "preform" may be flexible or rigid.

If an agent depot produced according to the present disclosure in sleeve form is used, the agent depot is preferably produced using a pure extrusion method, blow-molding method, or deep-drawing process. In rare cases, however, the agent depot is also produced by joining or gluing technology. For purposes of the present disclosure, joining technology, in the case of the sleeve, is defined as shrinking or joining "to fit" by pushing on, for example. If the sleeve only represents an intermediate step in the production of the medication carrier, the sleeve may also be slotted, lined on the interior with a bonding agent, and finally connected to the stent, e.g., by unrolling. Alternatively, the stent itself may be equipped with the bonding agent and then the stent may be connected to the slotted sleeve by unrolling, for example.

If an agent depot produced according to the present disclosure is used, in particular, for mechanical connection to an endovascular implantable stent, method step c) of the method according to one exemplary embodiment discussed herein additionally comprises the agent depot being cut to the length of a web and/or strut of the stent in sleeve form and the sleeve form being slotted along the axis. The sleeve thus processed represents a clip which is mechanically connectable to the webs and/or struts of the stent using force action and/or adhesive use, preferably in a form-fitting manner. Such a design is shown, in particular, in FIGS. 2a, 2b, 2c, 4a, and 4c.

If an agent depot produced according to the present disclosure in film form is used, the agent depot is preferably produced using an extrusion method, casting method, or rolling method. Films may also sometimes be drawn from a melt or solution.

The method according to the present disclosure for producing the agent depot preferably also comprises, in a method step c), the agent depot in film form being processed in such a manner that the film form is connected to i) the area of the abluminal surface of the body, preferably the stent, or ii) to a part thereof. A film may accordingly be attached around the entire stent and/or a strut of a stent and may, in particular, be attached as in FIG. 5a to the struts at the ends of an implantable stent. If a film is attached to the ends of an implant, preferably a stent, the film is to have a composition which does not project into the lumen and thus impair the unobstructed blood flow.

If the agent depot produced according to the present disclosure in film form is used for connection to an endovascular implantable stent, the film form i) or ii) of the agent depot used according to the present disclosure is preferably characterized in that the film may be provided perforated corresponding to the geometry of the abluminal surface of the stent, the film material corresponding to the areas of the material of the stent. The films described in FIGS. 5a and 5b may accordingly also be provided as perforated, for example, to allow the blood flow into the side branches of blood vessels.

Agent depots according to the present disclosure in film form may also be connected to the endovascular implantable body, preferably in a form-fitting manner, using suitable means, preferably C-shaped grippers, hooks, and the like. Such an exemplary embodiment is shown, in particular, in FIGS. 5a and 5b.

If the agent depot according to the present disclosure is produced as a preform, the agent depot is preferably characterized in that it represents a hollow body which is produced, for example, using a hollow body blowing method or injection-molding method, the preform representing the negative of a point of the implant, preferably a stent, to which it is to be attached.

If a preform is produced according to a method of the present disclosure for producing the agent depot, the preform may be applied to the body, preferably a stent, by gluing (FIGS. 7a-7d), clicking together (FIGS. 8a-8e), or by welding together the top and bottom sides and is thus mechanically connectable to the body, preferably a stent, preferably in a form-fitting manner.

Figure 4A:
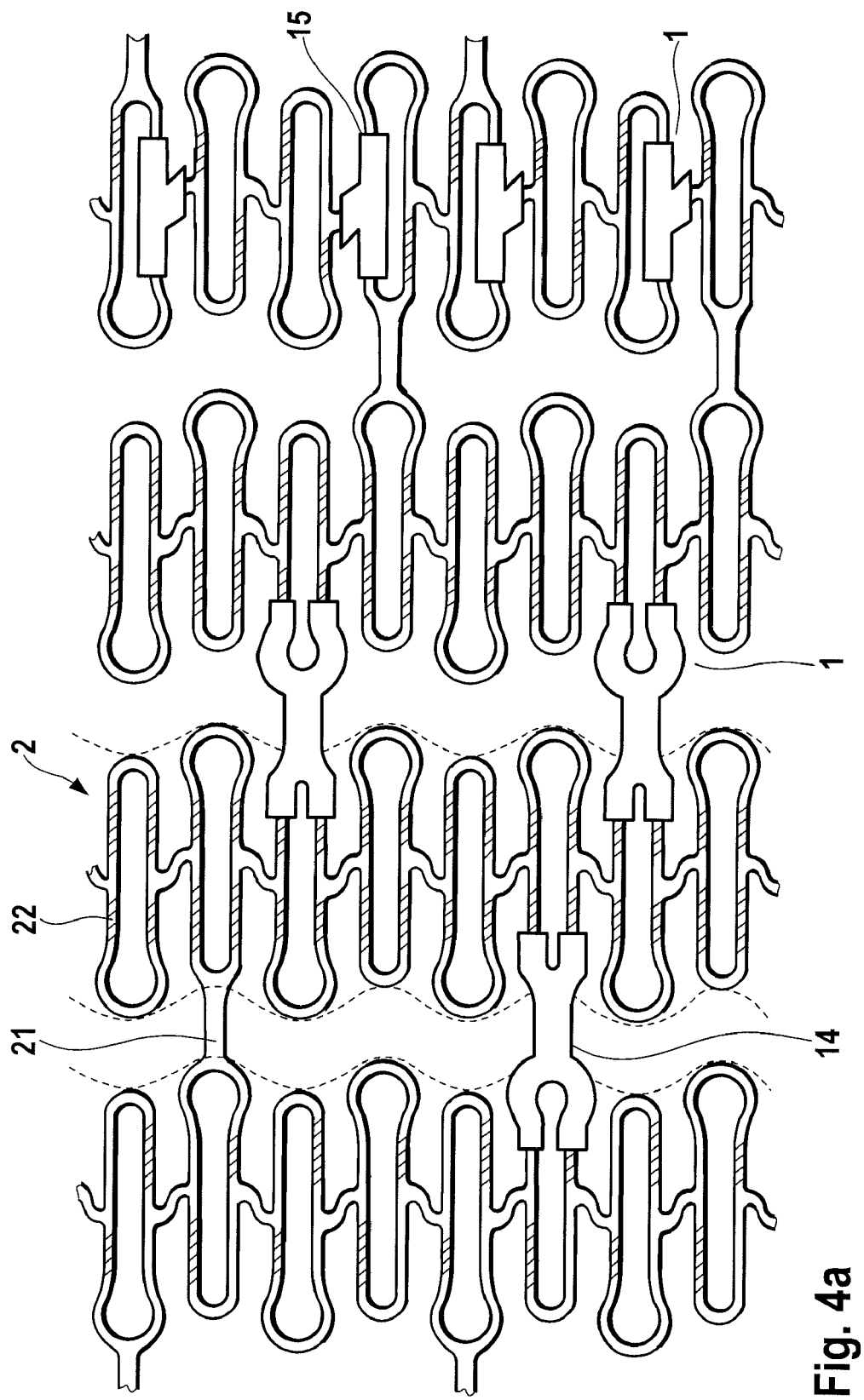
FIG. 4a is a top view of an abluminal detail of a stent geometry 2 having multiple agent depots 1, 14, and 15, which are clipped onto the abluminal surface on struts.
Figure 4B:
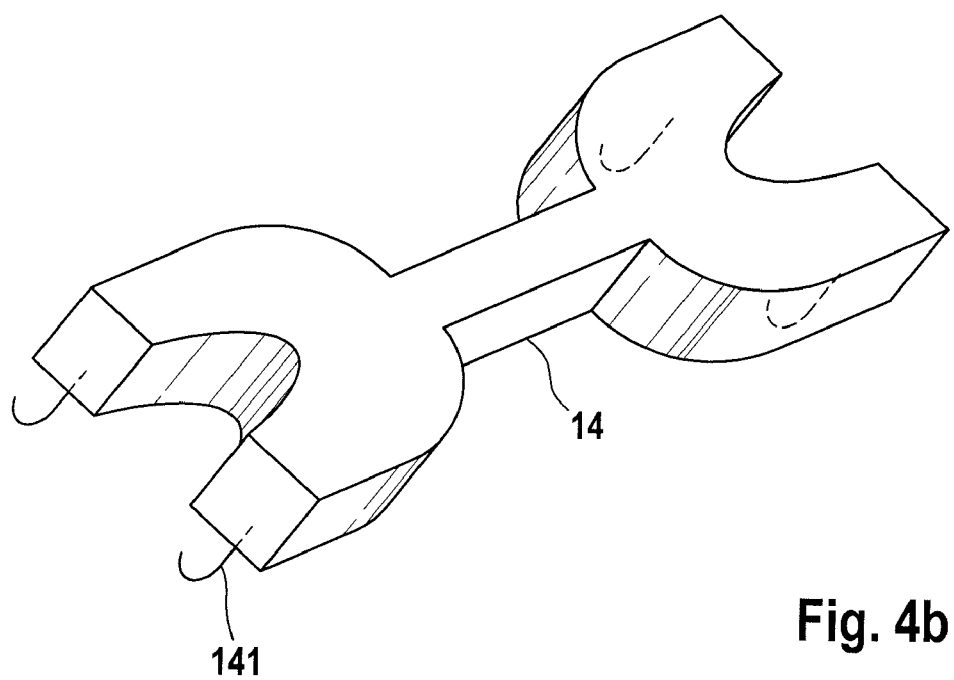
FIG. 4b is a perspective view of an agent depot 14.
Figure 4C:
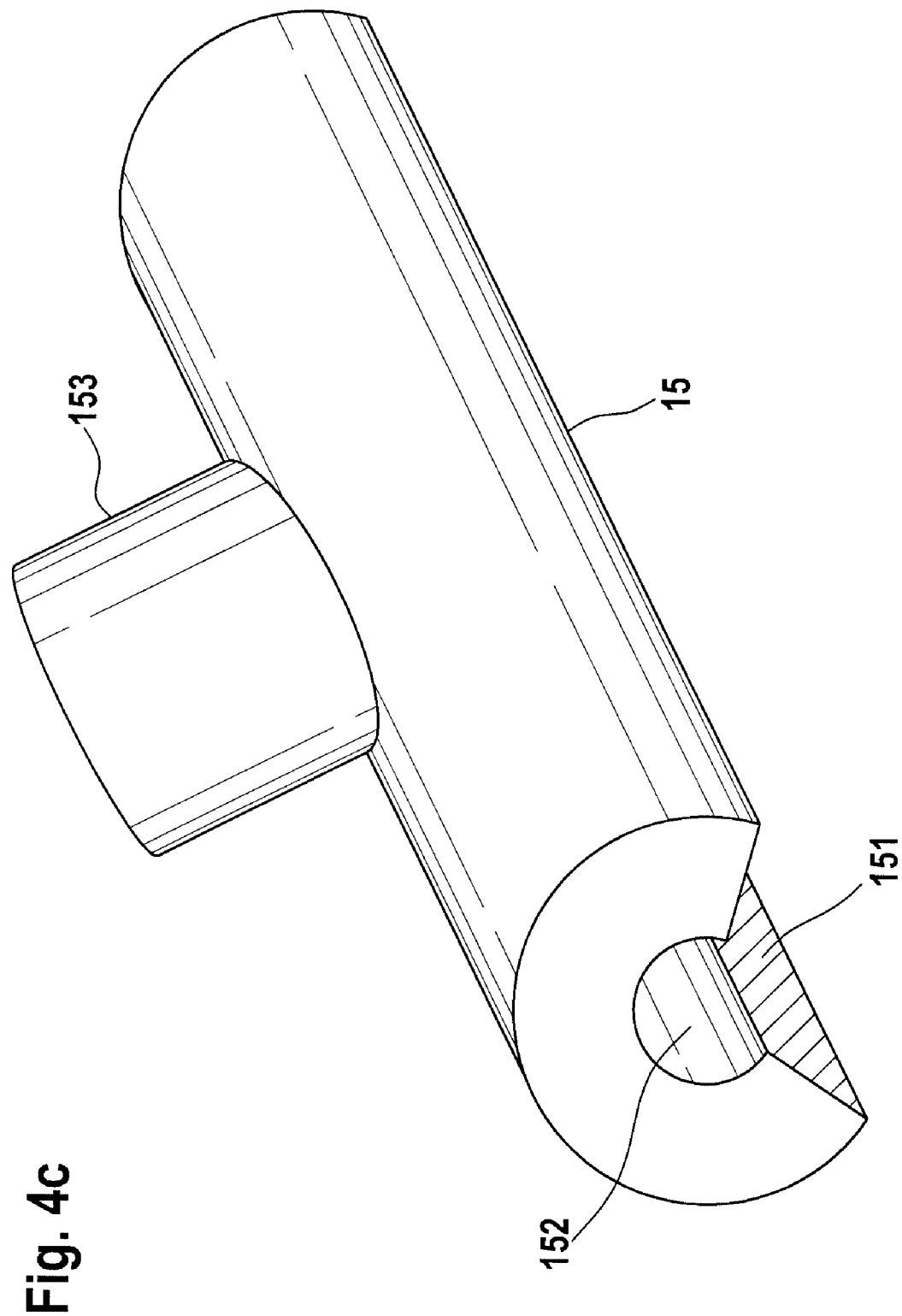
FIG. 4c is a perspective view of an agent depot 15.
Figure 4D:
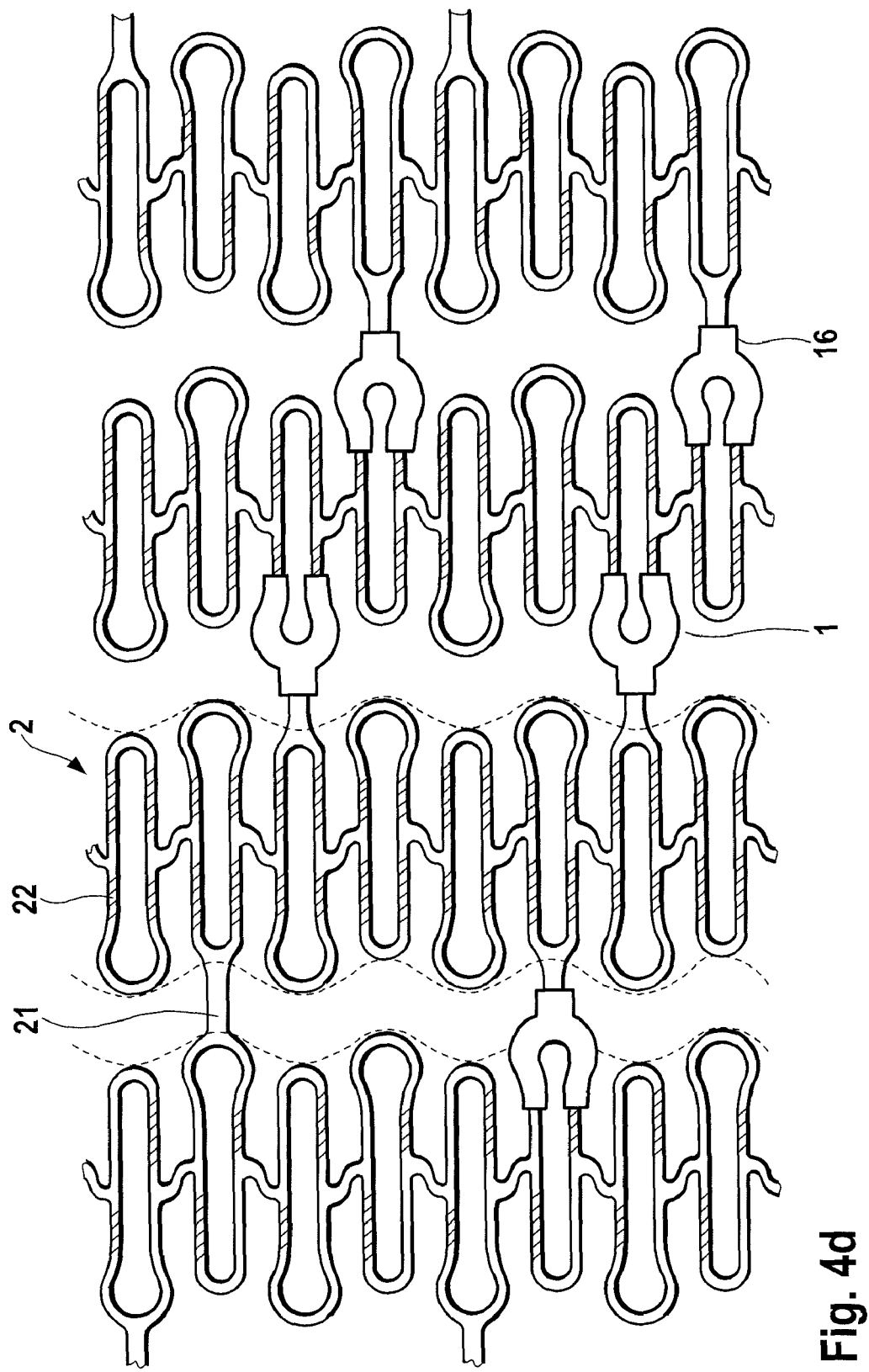
FIG. 4d is a top view of an abluminal detail of a stent geometry 2 having multiple agent depots 1 in slotted preform 16.
Figure 4E:
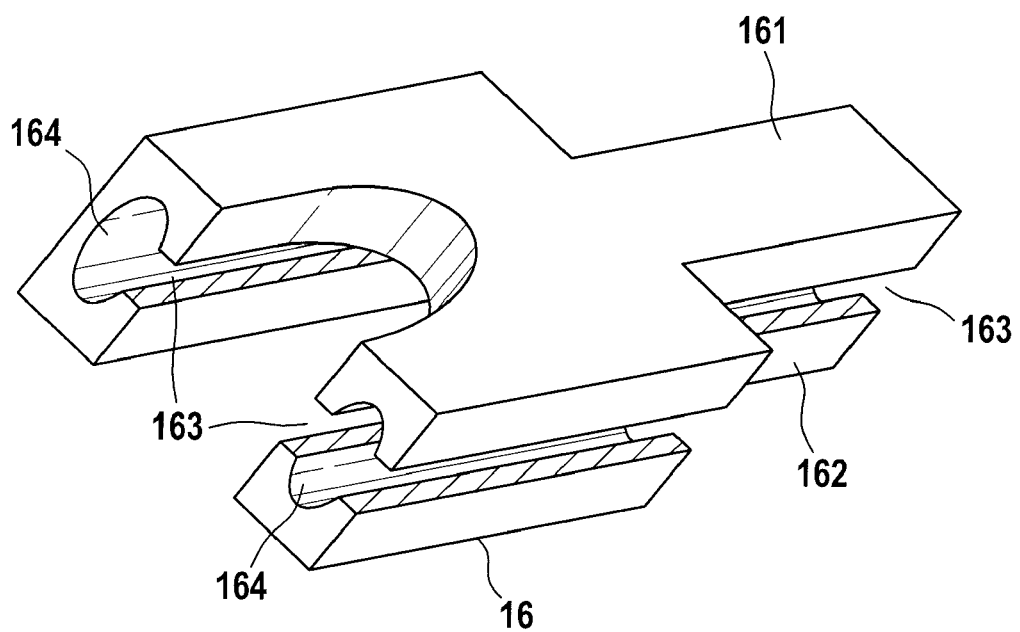
FIG. 4e is a perspective view of an agent depot 16.

If an agent depot is used as a preform for the connection to an endovascular implantable stent, the preform is preferably processed according to the present disclosure in such a manner that the preform is slotted along the axis or is already provided with a slot when the preform is cast and this preform represents a clip which is mechanically connectable to the stent using force action and/or adhesive use, preferably in a form-fitting manner (FIG. 4e).

If an agent depot is used as a preform for connection to struts of an endovascular implantable stent, the preform is processed according to the method of the present disclosure in such a manner that the preform is cut to the length of the webs and/or struts of the stent, slotted along the axis or already provided with a slot when the preform is cast, and this preform represents a clip which is mechanically connectable to the webs and/or struts of the stent using force action and/or adhesive, preferably in a form-fitting manner. Such an exemplary embodiment is shown in FIGS. 1a, 1b, 3b, 4c, 4e, and 5c.

The preform may alternatively comprise two parts which are then welded around the strut.

Agents which are preferably used for an agent depot produced according to the method of the present disclosure are suitable for prophylaxis or therapy of an in-stent restenosis or cancer treatment. Preferably used agents are selected from the group consisting of lipid regulators, immunosuppressives, vasodilators, calcium channel blockers, calcineurin inhibitors, antiphlogistics, anti-inflammatory agents, antiallergy agents, oligonucleotides, estrogens, endothelium producers, steroids, proteins, peptides, proliferation inhibitors, analgesics, antirheumatics, angiogenesis inhibitors, and cytostatics.

Other agents which may be used include Cytostatics, which particularly include DNA-alkylating substances, in particular nitrogen mustard compounds and nitrosourea compounds; platinum compounds; hydroxyurea compounds; anti-metabolites, preferably folic acid antagonists, purine analogs and pyrimidine analogs; microtubuli inhibitors, preferably Winker alkaloids, taxanes, preferably paclitaxel and dozetaxel; topoisomerase inhibitors; antibiotics, preferably anthracyclines, particularly preferably daunorubicin, doxorubicin, epirubicin, and idarubicin, anactinomycines, in particular dactinomycin, methoxanthrone, asarkrin, and ansarkrin, mitomycin C, and bleomycin; as well as greatly varying cytostatics from the group asparaginase, metefusin, and imatinib; hormones, preferably glucocorticoids, in particular prednisone, sexual hormones, particularly preferably estrogens, gestagens, gonadoliberine (GnRH), fludamid, bizalutamid, tamoxifen, and toremifen, aromatase inhibitors, such as aminoglutetimide, formestan, eksemistan, retrozol, and anastrozol; antibodies, immunomodulators and cytokines, preferably trastuzumab, cetiximab, rituximap, alemtuzumab, daklizumab, gemtuzumab, epratuzumab and ibritumomap; interleukin-II, interferon-α, tumor necrosis factor α (TNF-α), and hematopoietic growth factors, such as G-CSF, GM-CSF.

If an endovascular implantable body, preferably a stent, more preferably a degradable stent, is mechanically connected to an agent depot produced according to the method of the present disclosure, preferably in a form-fitting manner, the method preferably additionally comprises one of the bodies from step a) of the method being entirely or partially coated with one or more auxiliary agents before connection to the agent depot in step c), the auxiliary agents reinforce the mechanical connection of the agent depots to the body or bodies.

According to the present disclosure, adhesives are preferably used as the auxiliary agent, preferably pure plastic solvents, instant adhesives from the group consisting of acrylates, fibrin adhesives, fats, and polysaccharides.

According to a preferred exemplary embodiment of the method for the production of the endovascular implantable body charged with agent, preferably a (degradable) stent, if a sleeve form is used as the agent depot, the sleeve preferably corresponds to the length of a web or strut of the stent, is slotted along the axis, and thus represents a clip which is mechanically connected in method step c) using force action and/or adhesive use to the web or strut of the stent, preferably in a form-fitting manner.

If an agent depot produced according to the present disclosure in film form is used, preferably film i) or ii) being used, the endovascular implantable body, preferably a degradable stent, is unrolled having the abluminal surface on the film i) or ii) in step c) and is thus mechanically connected using force action and/or adhesive use, preferably in a form-fitting manner.

If a preform is used, the production method according to the present disclosure, the preform is glued, clicked (snap-fitted) together, or welded together in step c) onto the implantable body, and is thus mechanically connected to the body, preferably in a form-fitting manner.

Alternatively, the preform may also be attached to the implantable body by shrinkage with decentralized heat supply, so that the agents are not damaged.

Alternatively, an exemplary method according to the present disclosure for producing the agent-charged endovascular implantable body is characterized in that, in a further step, the preform is processed so that the preform is slotted along the axis or is already provided with a slot when cast and this preform represents a clip which is mechanically connected in step c) to the body, preferably a stent, using force action and/or adhesive use, preferably in a form-fitting manner.

The preform is preferably cut to the length of a web or a strut of the stent, slotted along the axis or already cast having a slot, so that the preform represents a clip which is mechanically connected in step c) to the web or strut of the stent using force action and/or adhesive use, preferably in a form-fitting manner.

Insofar as the agent-charged endovascular implantable body represents a stent producible according to a method of the present disclosure, the agent-charged endovascular implantable body is preferably a degradable endovascular implantable stent, especially preferably a degradable metal stent. The preferred designs described herein for the production method according to the present disclosure are to be applied to the present implantable body according to the present disclosure, preferably a degradable stent.

Insofar as the present disclosure relates to a kit, the preferred embodiments which relate to the agent depot or the endovascular implantable body are explained in greater detail by the preferred exemplary embodiments described of the production method according to the present disclosure.

Exemplary embodiments for the use according to the present disclosure of one or more agent depots for producing an agent-charged implantable body or for the method according to the present disclosure for prophylaxis or treatment of a stenosis, an aneurysm, or a tumor tissue may be achieved in that one or more of the above-mentioned preferred exemplary embodiments are received in the body. The agent or agents are attached especially for the particular therapy. The term agent is to be understood as comprising one or more agents.

A high concentration of agent(s) is preferably used for the prophylaxis or therapy of a tumor tissue. Accordingly, those agent depot forms which may contain a high concentration of agent are preferred for an exemplary embodiment according to the present disclosure. For example, suitable agent depots are shown in FIGS. 3a, 3b, 5a, 5b, and 5c. An agent-charged stent producible according to the present disclosure is preferably implanted in a blood vessel which carries blood to the tumor, preferably in proximity to the tumor tissue.

DETAILED DESCRIPTION

FIG. 1a shows an abluminal detail of a stent geometry 2 (the stent geometry is described in U.S. Pat. No. 6,896,695), together with multiple, preferably form-fitting, clipped-on agent depots 1 in the form of slotted beads 11 the agent depot beads 11 according to the present disclosure have a cavity and are slotted 111 in such a manner that the beads may be clipped, in particular, onto the longitudinal connectors (struts) 21 or alternatively onto the linear areas of the stent struts 22 (latter embodiment not shown), preferably in a form-fitting manner (see also FIG. 1b). Such a design according to the present disclosure is preferable for one or more agents which have a good distribution into the vascular tissue after release of the agent(s).

Due to the high proportion of a non-agent-charged stent main body 2, improved overgrowth with endothelial cells ("EC"; endothelialization) may be made possible in relation to typically completely coated stents from the prior art. Due to this improved endothelialization of the stent 2, the risk of a thrombosis which is connected to the implantation of an endovascular implantable body may also be reduced.

Figure 1B:
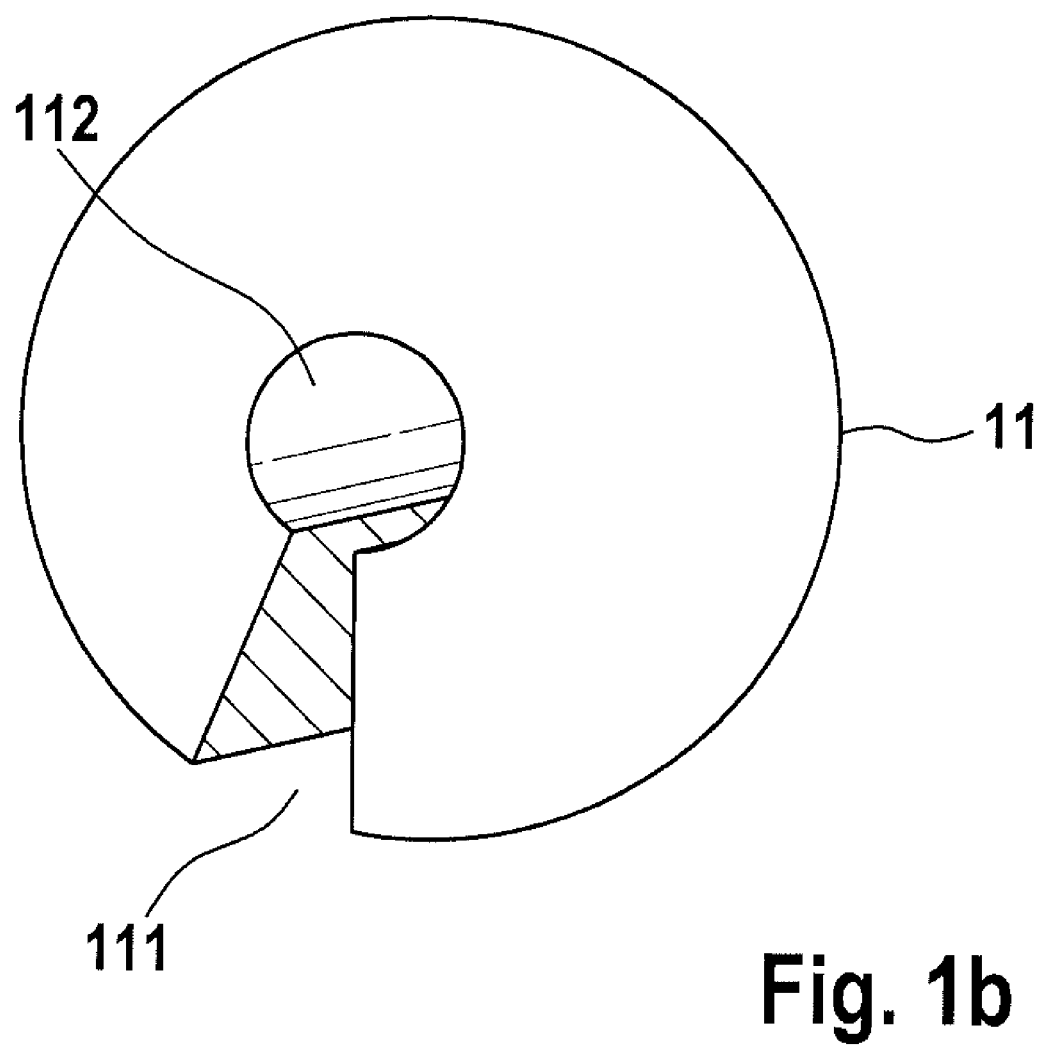
FIG. 1b is a perspective view of a slotted agent depot in bead form 11.

FIG. 1b shows a view of agent depot beads 11 according to one exemplary embodiment of the present disclosure having a slot 111 and a cavity 112, which is designed so that the agent depot beads may be clipped onto a strut 21 or web 22 of a stent 2, preferably in a form-fitting manner. These agent depot beads 11 may comprise one or more agents according to the present disclosure. The agent depot beads 11 used may also each comprise different concentrations of one or more agents.

Agent depots according to the present disclosure in the form of beads 11 are preferably produced using casting, film, and joining methods.

Figure 2A:
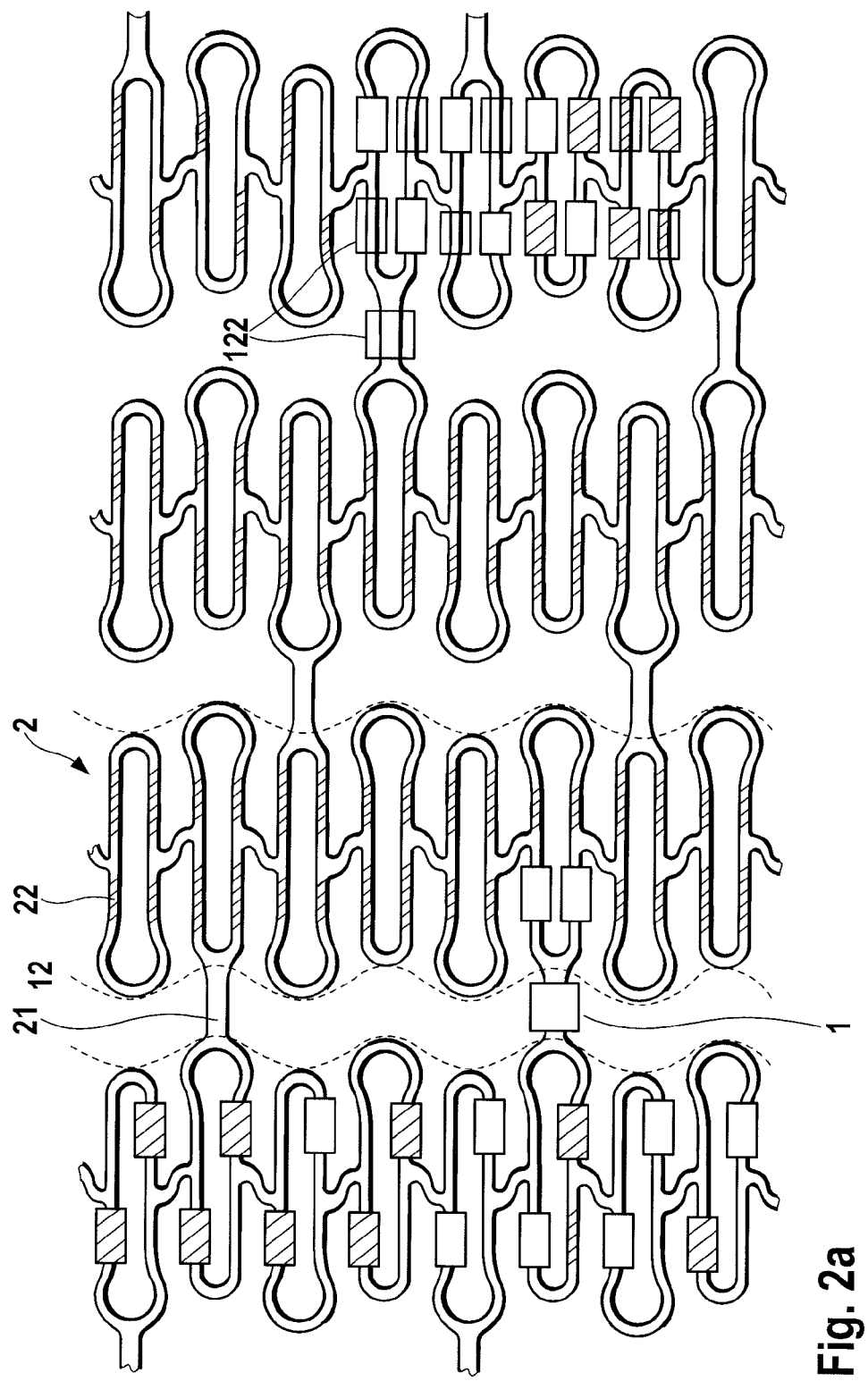
FIG. 2a is a top view of an abluminal detail of a stent geometry 2 having multiple agent depots 1 in sleeve form 12.

FIG. 2a shows an abluminal detail of a stent geometry 2 (which is described in U.S. Pat. No. 6,896,695) having multiple clipped-on agent depots 1 in sleeve form 12. The sleeves 12 are slotted 126 along the longitudinal side and have a cavity 127 to be able to be clipped, in particular, onto the longitudinal connectors (struts) 21 or alternatively onto the linear areas of the stent struts 22 of a stent 2, preferably in a form-fitting manner (see also FIG. 2c). Such an agent charge according to the present disclosure is preferably of interest for a surface-covering charge having two, three, or more agent depots (121, 122, and 123). A multiple drug release, in particular, a dual-drug release (release of two agents) or a triple-drug release (release of three agents) may thus be made possible.

Such a design is also preferable, in particular, for those agent depots whose polymer may not be connected according to typical coating methods to the main body of the stent or the implantable body because of a lack of suitable solvents or polymer adhesion to the stent material used.

Figure 2B:
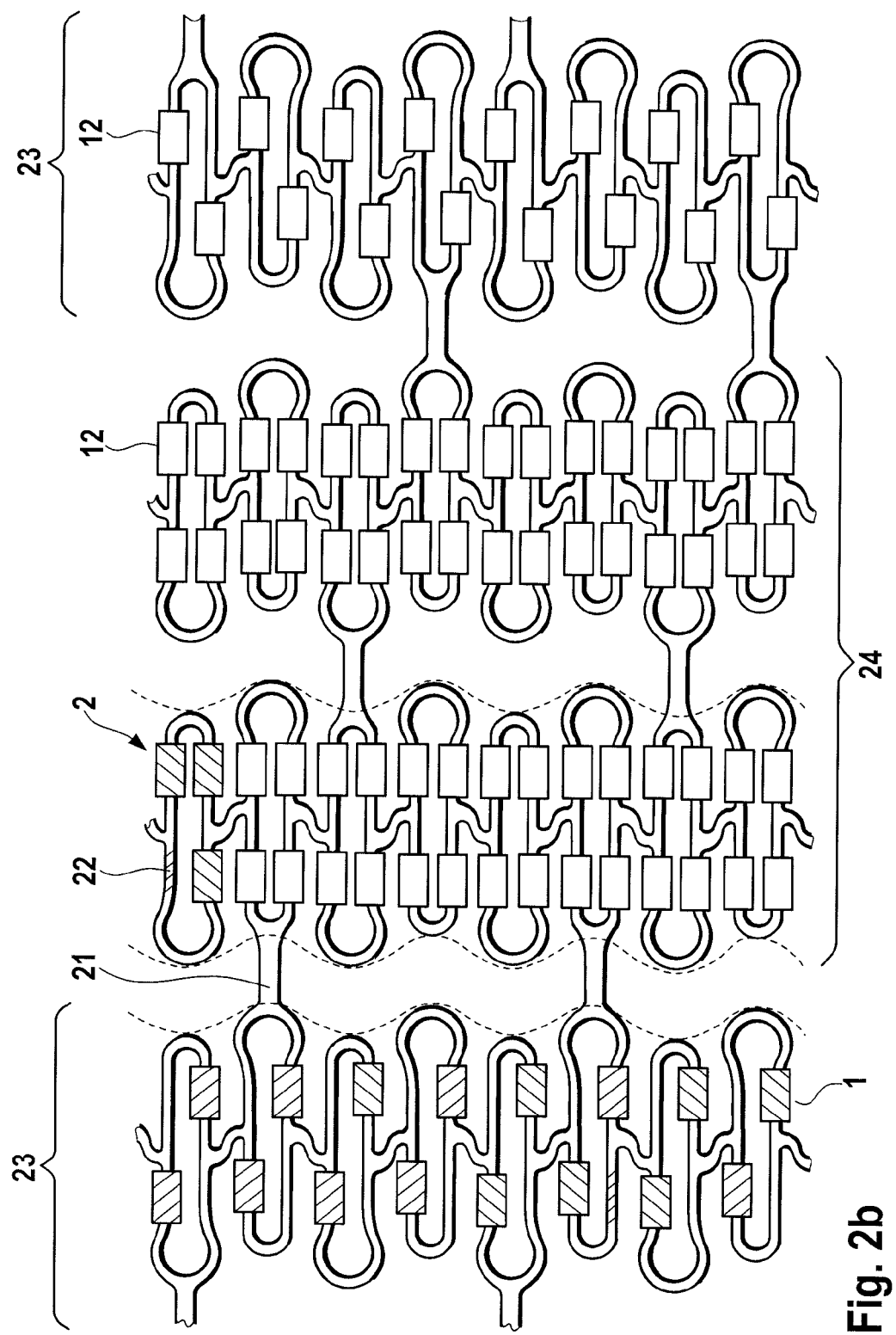
FIG. 2b is a top view of an abluminal detail of a stent geometry 2 having multiple agent depots 1 in sleeve form 12 having varying charge of agent depots over the longitudinal axis.

FIG. 2b shows a design as an alternative to FIG. 2a. In this design according to the present disclosure, the areas 23 of the stent have a lower charge of the agent depots 12, i.e., fewer agent depots 12 per unit area of the stent 2, in relation to the areas 24 of the stent. The agent depots 12 are preferably clipped in a form-fitting manner onto the web 22 or strut 21 of a stent 2.

FIG. 2c shows a view of the slotted agent depots according to one aspect of the present disclosure in sleeve form 12, a slot 124 and a cavity 125, which is designed in such a manner that it may be clipped onto a strut 21 or web 22 of a stent 2, preferably in a form-fitting manner. An agent depot 12 may typically contain one or more agents. Agent depots 121, 122, and 123 differ in that the agent depots each comprise a different agent.

Agent depots according to the present disclosure in sleeve form 12, 121, 122, and 123 are preferably produced using extrusion methods, blow-molding methods, and deep-drawing methods. In rare cases, joining or gluing technology is used.

Figure 3A:
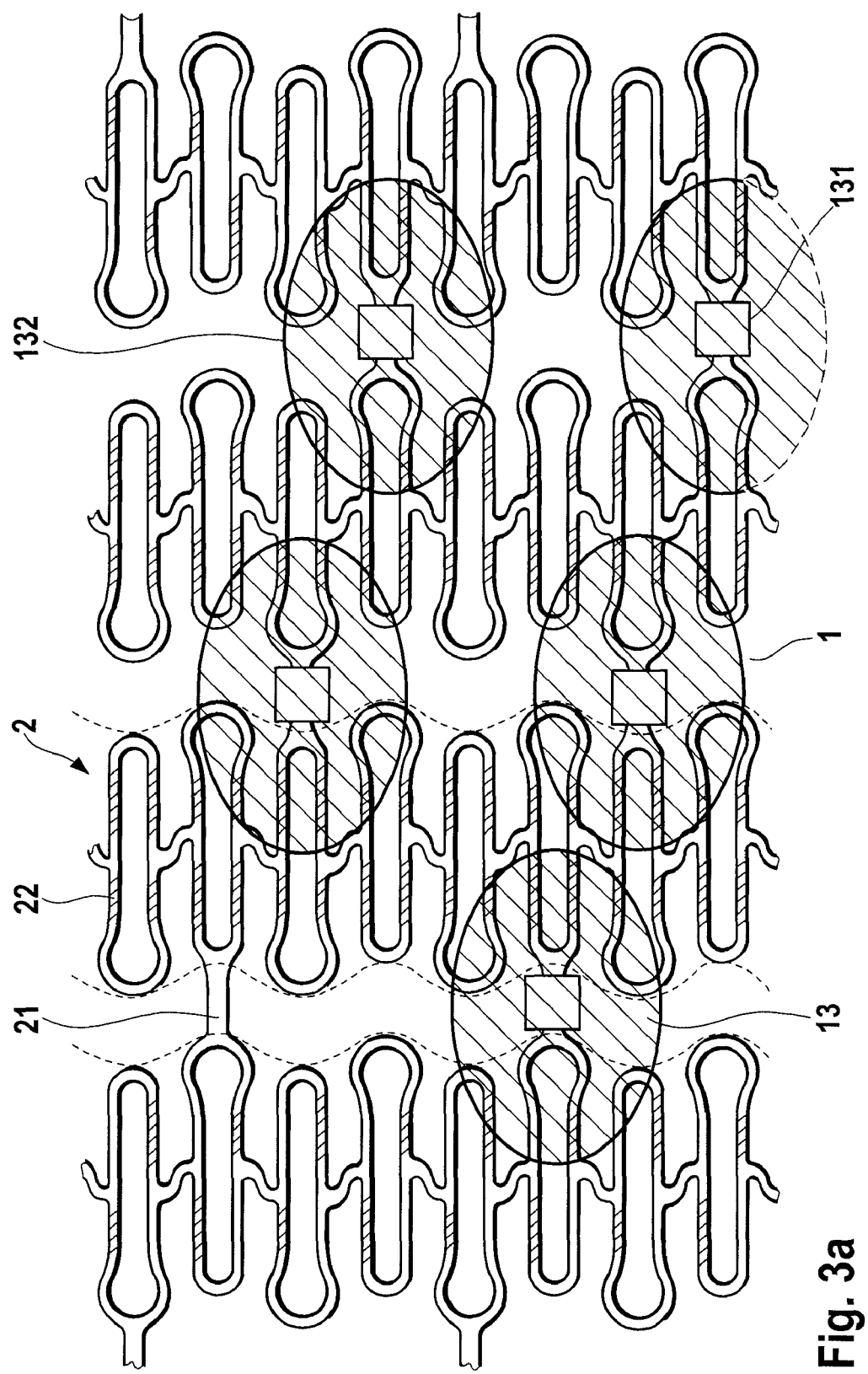
FIG. 3a is a top view of an abluminal detail of the stent geometry 2 having multiple flat slotted agent depots 1, 13 clipped onto struts.

FIG. 3a shows a view of an abluminal detail of a stent geometry 2 having multiple flat slotted agent depots 13 in preform, which are clipped onto struts 21 or webs 22 of a stent 2, preferably in a form-fitting manner.

Figure 3B:
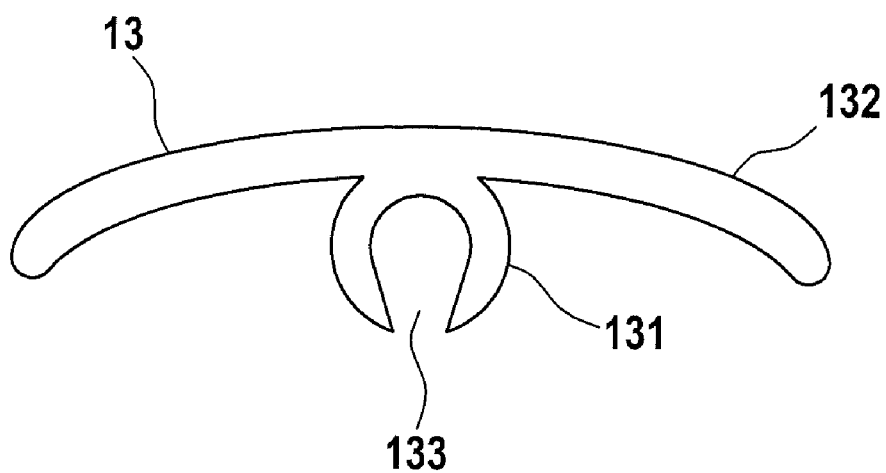
FIG. 3b is a perspective view of a flat slotted agent depot 13.

FIG. 3b, in particular, shows that the agent depot 13 according to the present disclosure is designed in such a manner that the agent depot comprises a C-shaped gripper 131 having slot 133, which may be clipped onto a strut 21 or web 22 of a stent 2, preferably in a form-fitting manner, and a matrix 132. Agent depots 13 according to the present disclosure comprise one or more agents and are preferably produced using casting methods, possibly combined with milling or plugging together or using a suitable joining method (hot gluing, gluing, for example) or injection-molding method.

A high agent concentration of the agent depot 13 is made possible using agent depot 13 shown in FIGS. 3a or 3b. The agent concentration is preferably localized in the matrix material 132 of the agent depot 13 which is situated on the abluminal surface of the implantable body, preferably a stent. In this way it is possible that little to no agent is discharged from the agent depot 13 into the vascular lumen from an implanted stent 2 and thus an endothelialization of the stent 2 is not delayed or prevented. The risk of a restenosis or a thrombosis is accordingly reduced according to the invention of the present disclosure.

FIG. 4a shows a top view of an abluminal detail of a stent geometry 2 having multiple agent depots 14 and 15 which are clipped onto the abluminal surface on struts. This design is comparable to the design according to the invention disclosed in FIG. 3a, with the difference that the agent depots 14 and 15, in contrast to the agent depot 13, are not clipped onto the struts 21 and webs 22 of the stent 2, rather, the agent depots are freely rotatable around the struts and webs of the stent. It is made possible by an exemplary embodiment shown in FIG. 4a that by using the agent depots 14 and 15 on the luminal surface of the charged stent 2, little polymer and/or agent of the particular agent depot 14 or 15 is present and thus an endothelialization of the implanted stent 2 is not decreased or prevented. The risk of a restenosis or thrombosis decreases accordingly.

FIG. 4b shows a perspective view of an agent depot 14 according to the present disclosure. The agent depot 14 comprises means 141 which are mechanically connectable to a strut 21 or a web 22 of a stent 2, preferably in a form-fitting manner. According to FIG. 4b, the means 141 particularly represent a hook shape. These means may be produced from the same material as the agent depot. An agent depot 14 according to the present disclosure is also preferably designed such that the agent depot at least partially covers the abluminal surface of a strut 21 and/or web 22 of the stent 2 in the clipped-on state. Little to no polymer, and preferably little agent-containing polymer of the agent depot 14 or 15, is preferably present on the luminal surface of the stent 2.

FIG. 4c shows a perspective view of an agent depot 15 according to one aspect of the present disclosure. Agent depot 15 is designed as a sleeve and/or preform. The agent depot has a slot 151 and a cavity 152 which may be clipped onto a strut 21 or web 22, preferably in a form-fitting manner. Furthermore, the agent depot 15 comprises material which covers the abluminal surface of a strut 21 or web 22 in the clipped-on state. In a preferred design, the slot 151 is wide enough that the agent depot 15 has little or no matrix material of the agent depot 15 on the luminal side in the state clipped onto the strut 21 or web 22 of the stent 2.

FIG. 4d shows a top view of an abluminal detail of a stent geometry 2 having multiple agent depots 16. The agent depots are designed such that, in the clipped-on state, the agent depots cover both the luminal and also the corresponding abluminal areas of one or more webs 22 and/or struts 21 of a stent 2, preferably in a form-fitting manner.

FIG. 4e shows a perspective view of an agent depot 16, which is designed so that, in the clipped-on state, the agent depot covers both luminal and also the corresponding abluminal areas of one or more webs 22 and/or struts 21 of a stent 2, preferably in a form-fitting manner. For this purpose, the agent depot 16 has an upper area 161 which preferably covers the abluminal surface of a stent 2, and a lower area 162, which preferably covers the luminal surface of a stent 2. In addition, an agent depot 16 according to the present disclosure has a slot 163 which allows the agent depot 16 to be clipped onto one or more webs 22 and struts 21. Preferably, an agent depot according to this aspect of the present disclosure comprises cavities 164 which enclose the webs 22 and struts 21 of a stent 2 in the clipped-on state, preferably in a form-fitting manner. One or more agents are preferably incorporated solely in the area 161 of the agent depot. This has the advantage that, due to a decreased discharge of the agents to the vascular lumen, the endothelialization of the stent 2 is not decreased or prevented.

Figure 5A:
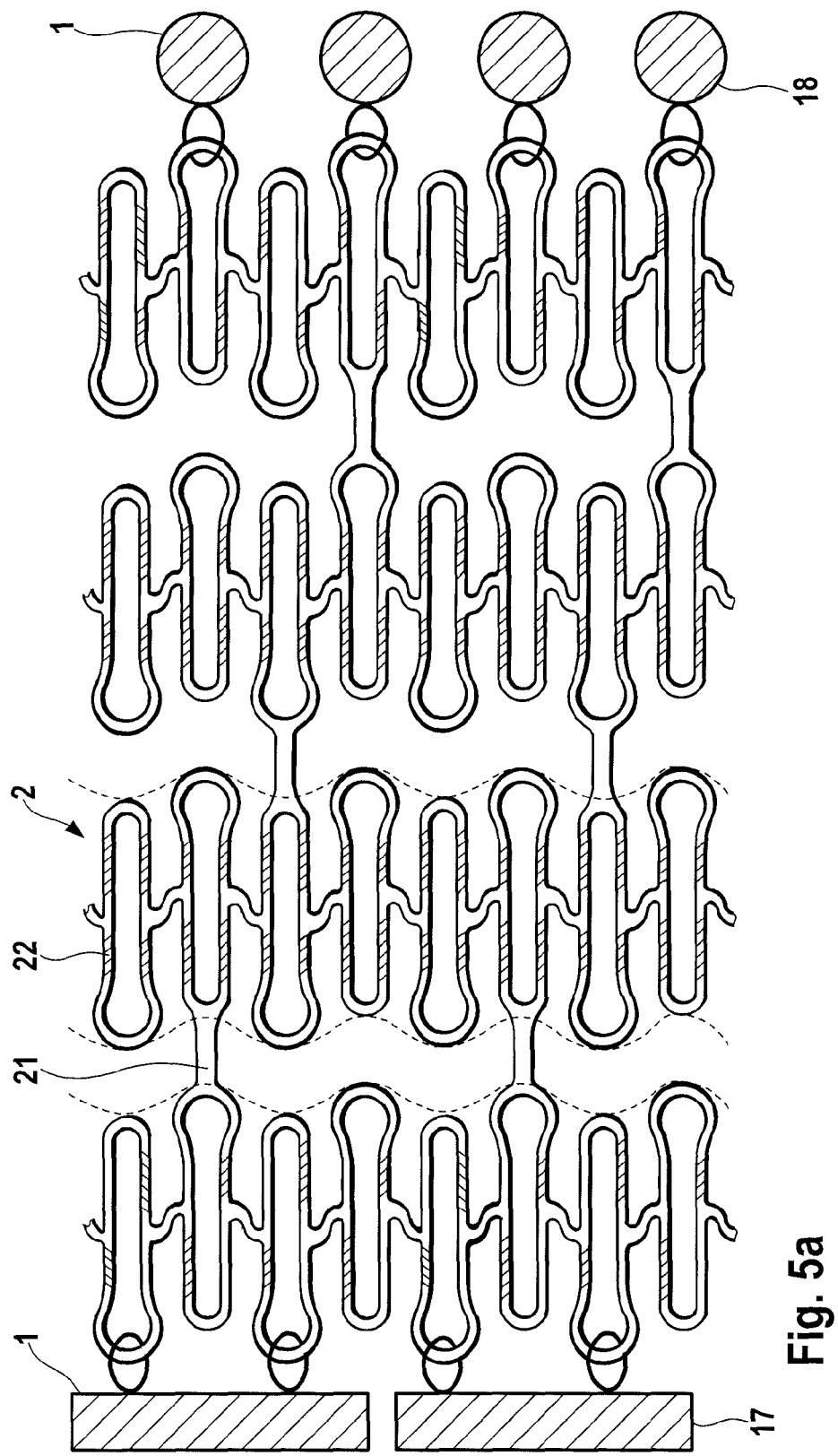
FIG. 5a is a top view of an abluminal detail of a stent geometry 2 having terminal agent depot 1 in the form of a clipped-on strip 17 or body 18.

FIG. 5a shows a top view of an abluminal detail of a stent geometry 2 having terminal, preferably form-fitting, clipped-on agent depots in the form of a strip 17 or a body 18. Such an exemplary embodiment according to the present disclosure is more rarely used for an antiproliferative use of a drug-eluting stent (DES), but rather preferably for the release of agents, in particular, selected from the group of cytostatics into the bloodstream for treating tumors. In this exemplary embodiment according to the present disclosure, the stent is not used because of its support structure, but rather is used as an anchor for the agent depots 17 and 18. A stent charged in this manner is preferably implanted in a blood vessel which carries blood to the tumor tissue, preferably in proximity to the tumor tissue. In this way, it is possible for the highest possible concentration of agent used to reach the tumor tissue.

Figure 5B:
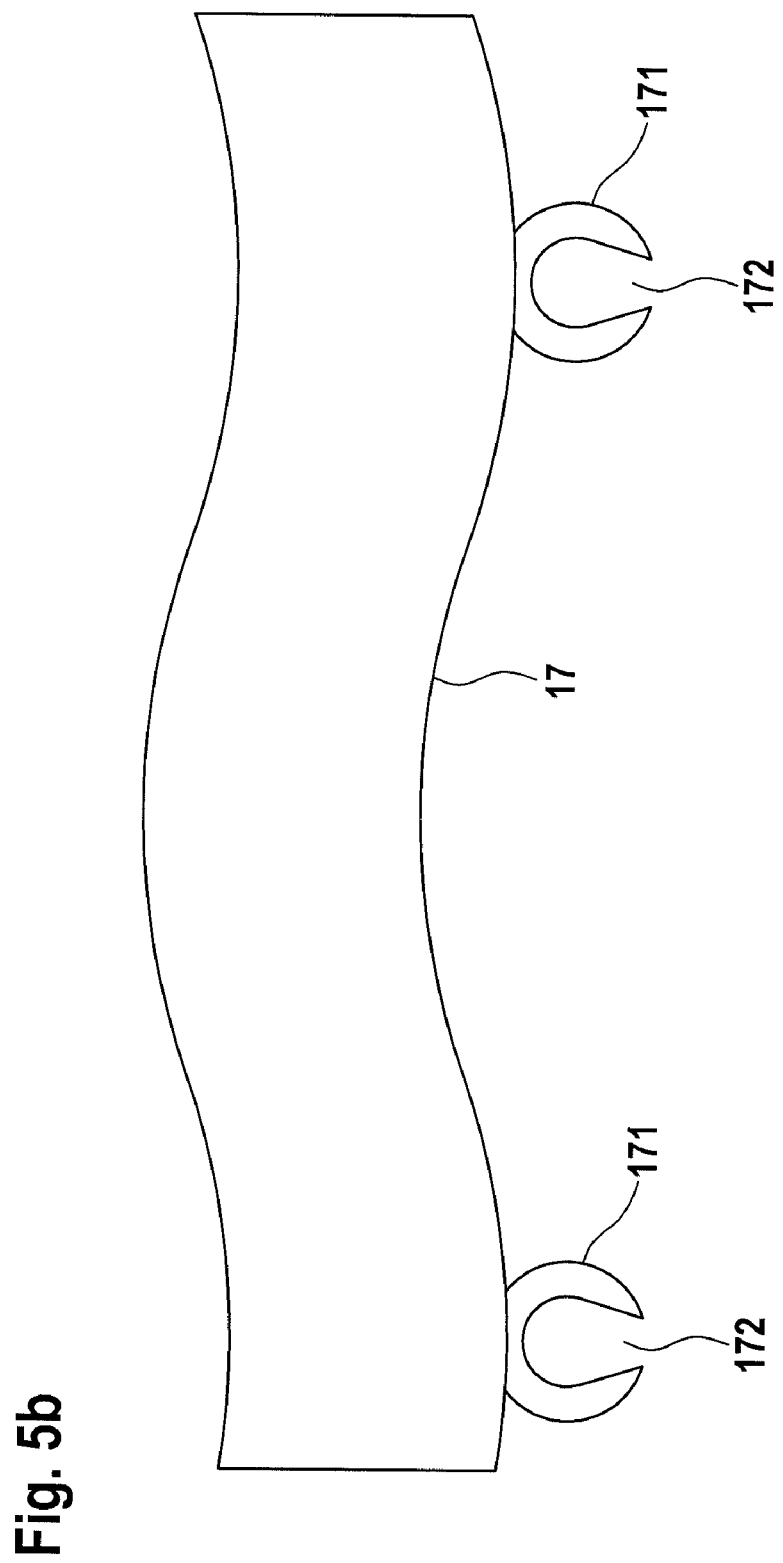
FIG. 5b is a perspective view of an agent depot in strip form 17.
Figure 6A:
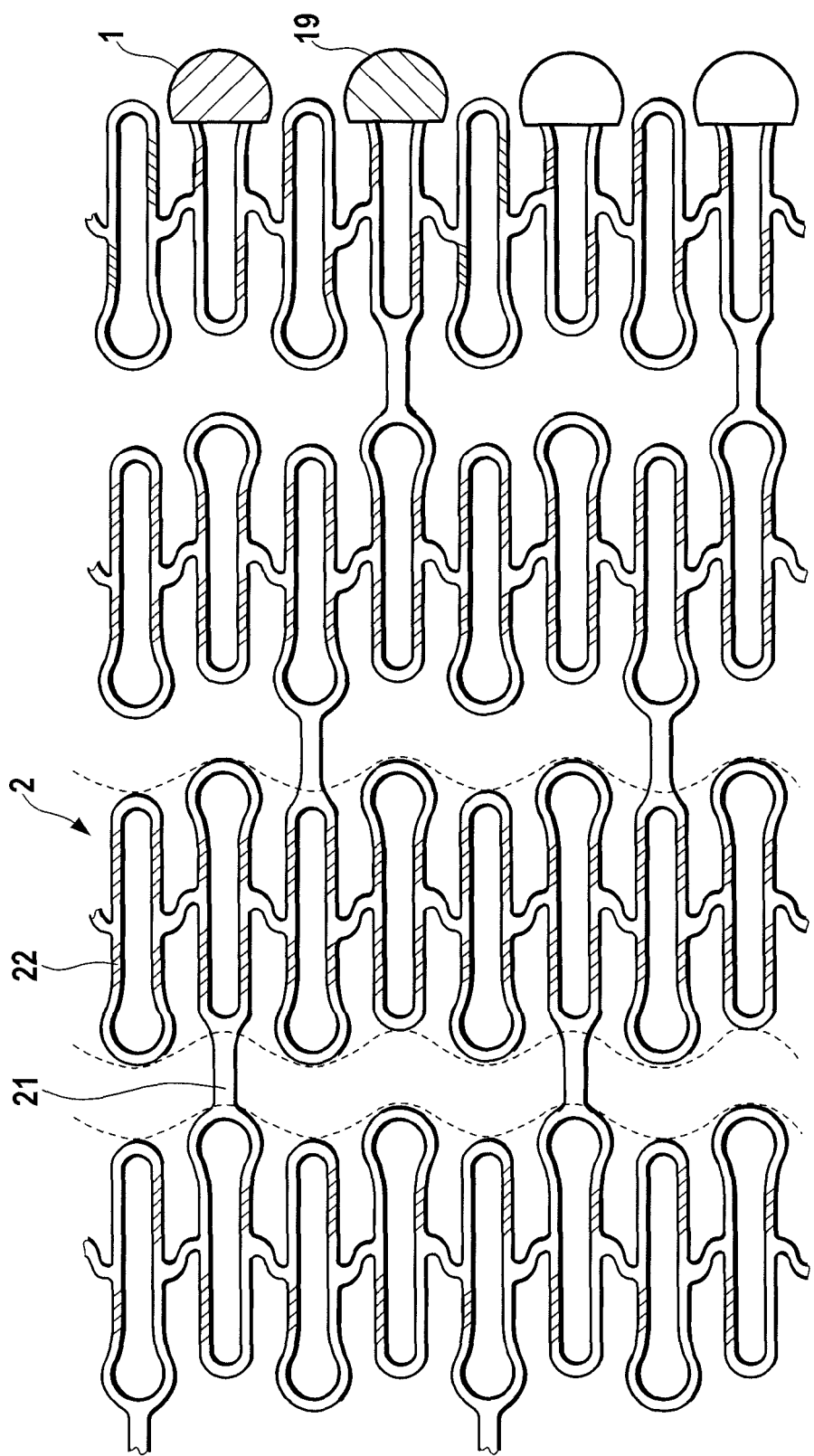
FIG. 6a is a top view of an abluminal detail of a stent geometry 2 having multiple agent depots 1, 19, which are attached to the terminal arcs of the webs of the stent 2.
Figure 6B:
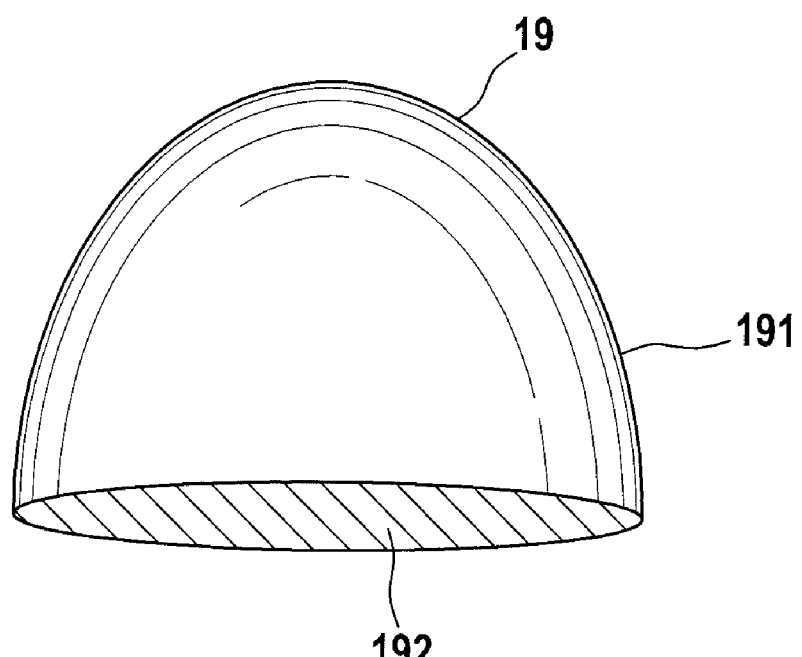
FIG. 6b is a perspective view of an agent depot 19 in preform.

FIG. 5*b* shows a perspective view of an agent depot according to the present disclosure in strip form 17. The strip 17 also has means 171 which allow the strip 17 to be mechanically connected to an endovascular implantable body, preferably a stent. Preferably, means 171 in the form of a C-shaped gripper having a slot 171 are used. In the clipped-on state the C-shaped gripper 171 encloses a web 22 or a strut 21 of a stent 2, preferably in a form-fitting manner. This agent depot 17 may comprise one or more agents.

Figure 5C:
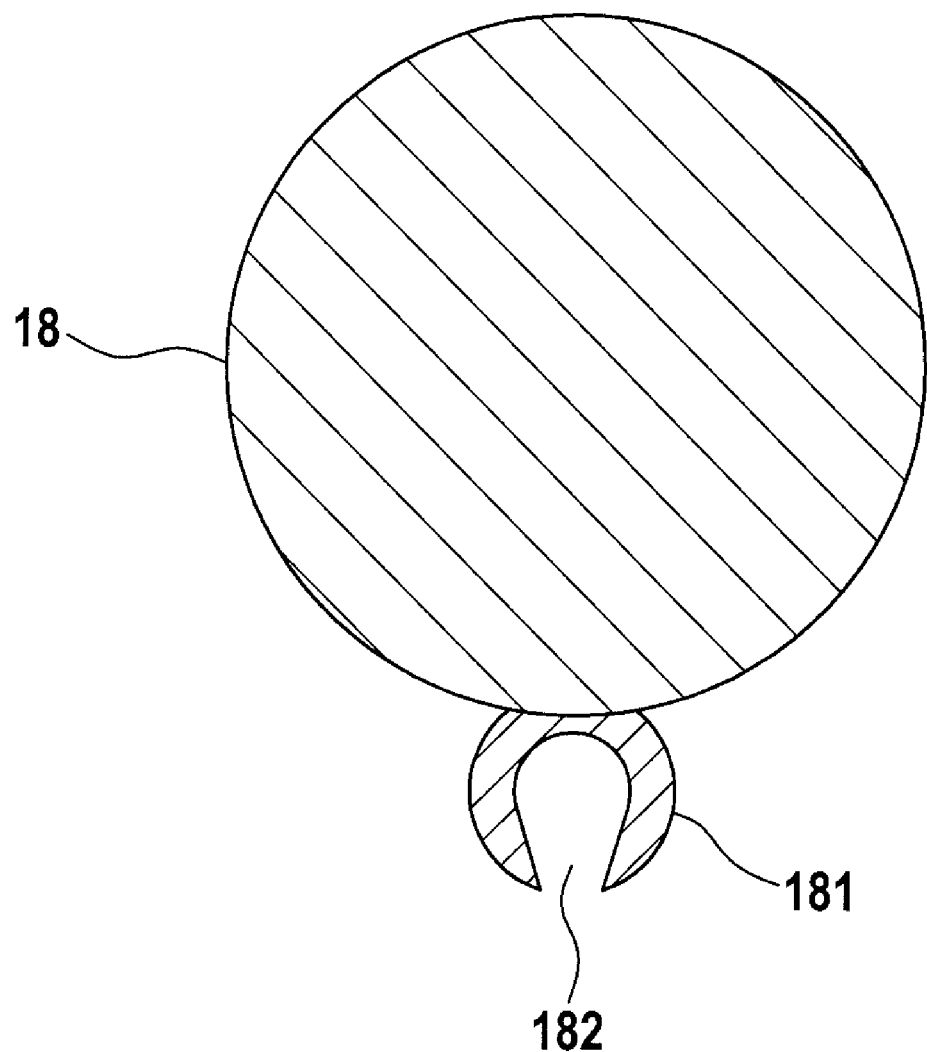
FIG. 5c is a cross-section view of an agent depot in the form of a body 18.

FIG. 5*c* shows a cross-section of an agent depot in the form of a body 18. The body 18 also has means 181 which allow the body 18 to be able to be mechanically connected to an endovascular implantable body, preferably a stent. Preferably, means 181 in the form of a C-shaped gripper which has a slot 181 are used. In the clipped-on state, the C-shaped gripper 181 encloses a web 22 or a strut 21 of a stent 2, preferably in a form-fitting manner. This agent depot 18 may comprise one or more agents. The C-shaped gripper may be produced, for example, using injection molding, reservoir, by joining methods (gluing, fusion, for example) or according to suitable other methods described hereinabove.

FIG. 6*a* shows a top view of an abluminal detail of a stent geometry 2 having terminally attached agent depots 19 in cap form, which are shrunk onto the webs 22 of a stent 2, preferably in a form-fitting manner. The agent depots 19 are preferably shrunk onto the round terminal areas of the stent 2 with decentralized heat supply so as not to damage the agents.

FIG. 6*b* shows a perspective view of an agent depot 19 having the surface 191 toward the vascular lumen or toward the vascular tissue and the internal surface 192 toward the webs 22.

Figure 7A:
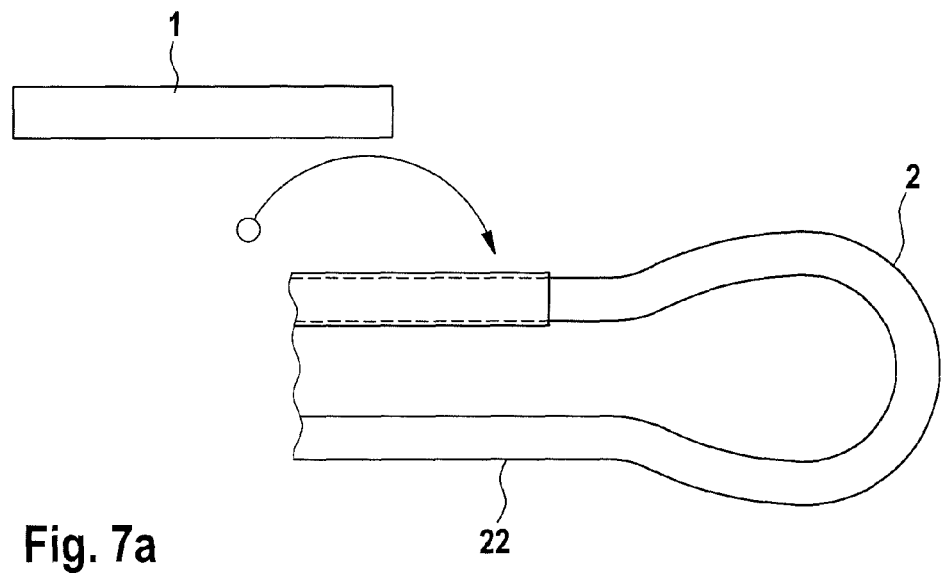
FIG. 7a is a schematic view of how an agent depot 1 is glued onto a stent strut 22 of a stent 2.

FIG. 7*a* shows a schematic abluminal view of a detail of the stent geometry 2 having stent struts 22 and an agent depot 1 in film form which is glued onto the stent struts 22, preferably using instant adhesives from the group consisting of acrylates, fibrin adhesives, fats, or polysaccharides. Alternatively, the agent depot 1 may have concave points and thus be glued in a form-fitting manner onto the stent struts 22.

Figure 7B:
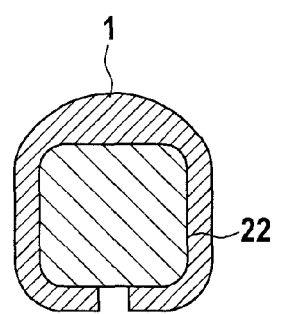
FIG. 7b is a cross-section view of a stent strut 22 having glued-on agent depot 1.

FIG. 7*b* shows a cross-section of a stent strut 22 having an agent depot 1 in film form.

Figure 7C:
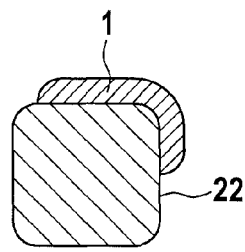
FIG. 7c is a cross-section view of a stent strut 22 having abluminal glued-on agent depot 1.

FIG. 7*c* shows a cross-section of a stent struts 22 having agent depot 1, the agent depot is situated on the abluminal surface of the stent strut 22 and correspondingly only a small component of the agents which is contained in the agent depot 1 being discharged to the vascular lumen. This is advantageous because the endothelialization of the stent is thus encouraged and the side effects of the stent as a foreign body are reduced.

Figure 7D:
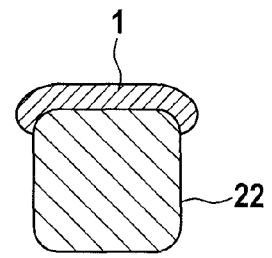
FIG. 7d is a cross-section view of a stent strut 22 having abluminal glued-on agent depot 1.

FIG. 7*d* also shows a cross-section of a stent strut 22 having agent depot 1 which is also situated on the abluminal side of the stent strut. Only small quantities of agent are discharged from the agent depot 1 to the vascular lumen. The advantages as described for FIG. 7*c* also exist here.

Figure 8A:
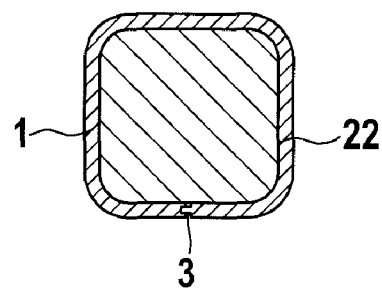
FIG. 8a is a cross-section view of a stent strut 22 having an agent depot 1 having connection mechanism 3.

FIG. 8*a* shows a cross-section of a stent strut 22 having an agent depot 1 enclosing the stent strut and connection mechanism 30.

Figure 8B:
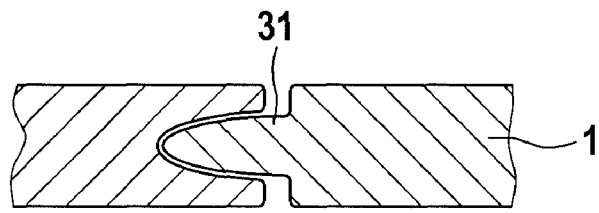
FIG. 8b is a schematic view of the connection mechanism 31 of the agent depot 1.

FIG. 8*b* shows the connection mechanism 31 of the agent depot 1 in an enlarged form. The connection mechanism 31 is a notch which may be introduced by milling into the agent depot at one end of the agent depot and a protrusion which is suitable for being plugged fitting into the notch at the diametrically opposite second end of the agent depot to thus cause a solid connection of the two ends of the agent depot.

Figure 8C:
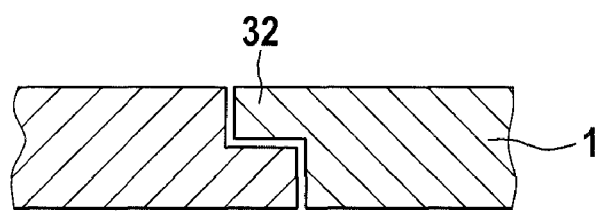
FIG. 8c is a schematic view of the connection mechanism 32 of the agent depot 1.

FIG. 8*c* shows the connection mechanism 32 of the agent depot 1 in enlarged form. The connection mechanism 32 is a connection mechanism having an L-shape, the diametrically opposite ends of the agent depot each having mirror-reversed L-shaped ends which may be plugged fitting into one another and thus cause a solid connection of the ends of the agent depot 1.

Figure 8D:
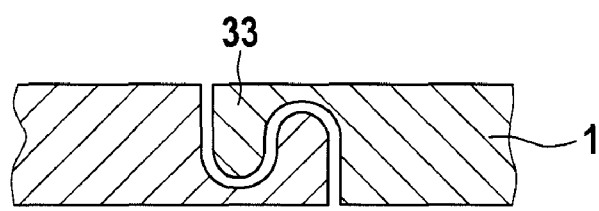
FIG. 8d is a schematic view of the connection mechanism 33 of the agent depot 1.

FIG. 8*d* shows a connection mechanism 33 of the agent depot 1 in enlarged form. The connection mechanism 33 is characterized in that the two diametrically opposite ends of the agent depot 1 are each provided in hook form and may be hooked in one another and thus cause a solid connection of the ends of the agent depot 1.

Figure 8E:
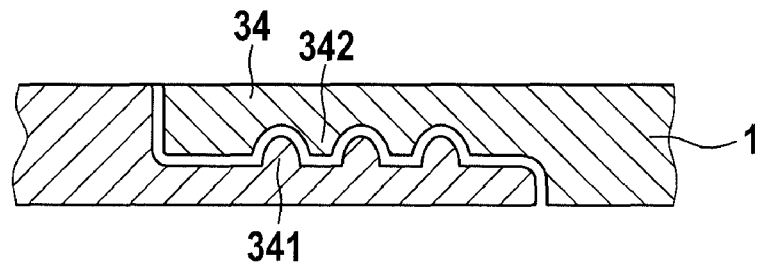
FIG. 8e is a schematic view of the connection mechanism 34 of the agent depot 1.

FIG. 8*e* shows a connection mechanism 34 of the agent depot 1 in enlarged form. The connection mechanism 34 fundamentally corresponds to the connection mechanism in L-shape, as is already described in FIG. 8*c*, but the connection mechanism 34 differs in that the face 341 has protrusions and the face 342 has corresponding notches which press against one another and thus cause a solid connection of the ends of the agent depot 1.

Figure 9A:
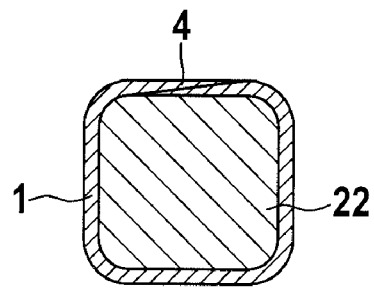
FIG. 9a is a cross-section view of a stent strut 22 having agent depot 1 and overlap area 4.

FIG. 9*a* shows a cross-section of a stent strut 22 having agent depot 1 which is situated overlapping in the area 4. This type of the connection may be attached in the position 4 either by the intrinsic tension of the agent depot 1 or by a suitable adhesive. Exemplary adhesives such as acrylates, fibrin adhesives, fats, and polysaccharides are suitable as preferred adhesives.

Figure 9B:
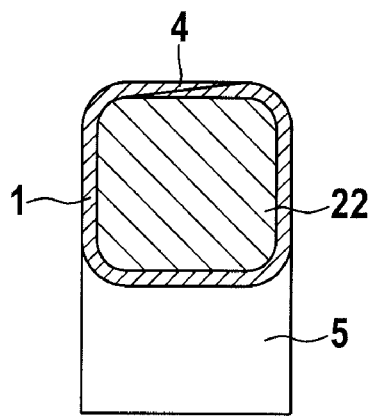
FIG. 9b is a cross-section view of agent reservoir 5, which is situated on the abluminal side.

FIG. 9*b* shows a cross-section of a stent strut 22 having agent depot 1, which overlaps in the area 4 and a further agent reservoir 5 which is preferably situated on the abluminal side. In this exemplary embodiment, the agent depot 1 preferably has no agent. The agent depot is put into its shape either by intrinsic tension or by additional gluing in the area 4. In this design, the reservoir 5 of the agent depot 1 has one or more agents, preferably antiproliferative agents.

Figure 9C:
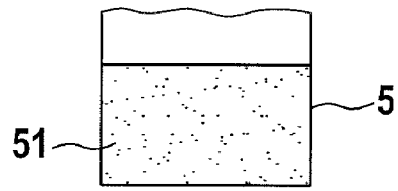
FIG. 9c is a schematic view of the agent reservoir 5.

FIG. 9*c* schematically shows a cross-section of the agent reservoir 5 of the agent depot 1, as shown in FIG. 9*b*, now as an agent reservoir 51 having a homogeneous agent distribution of one or more agents.

Figure 9D:
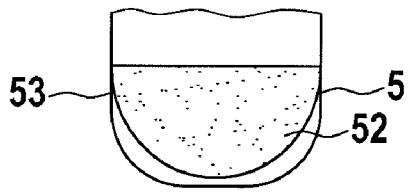
FIG. 9d is a schematic view of the agent reservoir 5.

FIG. 9*d* shows the agent reservoir 5 of the agent depot 1 from FIG. 9*b* as the reservoir 52, the agent being distributed homogeneously and a top coat 53 being coated over this layer, which influences the release of the agents in the reservoir 52.

Figure 9E:
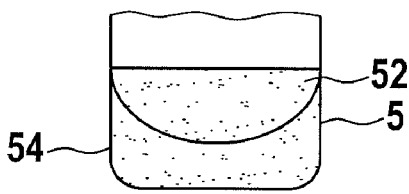
FIG. 9e is a schematic view of the agent reservoir 5.

FIG. 9*e* shows an agent reservoir 5 of an agent depot 1 from FIG. 9*b* in a preferred design. The reservoir 52 contains a homogeneous distribution of an agent and the reservoir 54 contains a homogeneous distribution of a further agent. A dual-drug application is thus made possible.

All patents, patent applications and publications referred to herein are incorporated by reference in their entirety.

What is claimed is:

1. A method for producing an agent depot for mechanical connection to a surface of an endovascular implantable body, comprising:
   a) providing one or more polymers;
   b) providing one or more agents; and
   c) producing at least one agent depot from the polymers and the agents, the at least one agent depot being mechanically connectable to the surface of the body using either force action or adhesive.

2. The method of claim 1, wherein at least one of the polymers represents either nondegradable or degradable polymers and at least one of the polymers is selected from the group consisting of: nondegradable polymers: polyethylene;

polyvinylchloride; polyacrylates; preferably polyethyl- and polymethylacrylates, polymethylmethacrylate, polymethyl-co-ethyl-acrylate, and ethylene/ethylacrylate; polytetrafluoroethylene, preferably ethylene/chlorotrifluoroethylene copolymers; ethylene/tetrafluoroethylene copolymers; polyamides; polyamide imide, PA-11, PA-12, PA-46, PA-66; polyetherimide; polyethersulfone; poly(iso)butylene; polyvinylchloride; polyvinylfluoride; polyvinylalcohol; polyurethane; polybutylene terephthalate; silicones; polyphosphazene; polymer foams; polymer foams made of carbonates, styrenes; copolymers and blends of the listed polymer classes; polymers of the class of thermoplastics; degradable polymers: polydioxanone; polyglycolide; polycaprolactone; polylactides, preferably poly-L-lactide, poly-D,L-lactide, and copolymers and blends thereof; poly(L-lactide-co-glycolide), poly(D,L-lactide-co-glycolide), poly(L-lactide-co-D,L-lactide), poly(L-lactide-co-trimethylene carbonate); triblock copolymers; polysaccharides; chitosan, levan, hyaluronic acid, heparin, dextran, cellulose; polyhydroxyvalerate; ethylvinylacetate; polyethylene oxide; polyphosphorylcholine; fibrin; albumin; polyhydroxy butyric acid; atactic, isotactic, and syndiotactic polyhydroxy butyric acid and their blends.

3. The method of claim 1, wherein the at least one agent depots is produced in step c) in either sleeve form, film form, preform, or as a net, the sleeve form is produced using either a pure extrusion method, blow-molding method, or deep-drawing process and the at least one agent depot in film form is produced using either an extrusion method, casting method, or rolling method.

4. The method of claim 3, further comprising, in method step c), that the at least one agent depot in sleeve form, the sleeve form having an axis, is brought to the length of either a web or a strut of the implantable body, the sleeve form is slotted along the axis, and the sleeve represents a clip which is mechanically connectable to either the webs or the struts of the endovascular implantable body using either force action or adhesive.

5. The method of claim 3, wherein the at least one agent depot is a preform of a hollow body in sleeve form, produced using either a hollow body blowing method or an injection-molding method, the preform represents a negative of a point of either the stent or web or the strut of the stent to which it is attached, and the preform is either glued, clicked together, or welded together from two or more parts onto the body and is mechanically connectable to the body.

6. The method of claim 5, wherein the preform is either already slotted or is slotted along the axis in a further step, said preform represents a clip which is mechanically connectable to the stent using either force action or adhesive, and said preform is cut to the length of either the web or the strut of the stent, is either already slotted or is slotted along an axis in a further step, and said preform represents a clip which is mechanically connectable to either the webs or the struts of the stent using either force action or adhesive.

7. The method of claim 1, wherein the one or more agents are suitable for either prophylaxis or treatment of either an in-stent restenosis or a cancer treatment, and the agents are selected from the group consisting of lipid regulators, immunosuppressives, vasodilators, calcium channel blockers, calcineurin inhibitors, antiphlogistics, anti-inflammatory agents, antiallergy agents, oligonucleotides, estrogens, endothelium producers, steroids, proteins, peptides, proliferation inhibitors, analgesics, antirheumatics, angiogenesis inhibitors, and cytostatics.

8. A method for producing an agent-charged endovascular implantable body, comprising the steps of:

a) providing an endovascular implantable body;
b) providing one or more different agent depots which are produced by
  (i) providing one or more polymers;
  (ii) providing one or more agents; and
  (iii) producing at least one agent depot from the polymers and the agents, the at least one agent depot is mechanically connectable to the surface of the endovascular implantable body using either force action or adhesive; and
c) mechanically connecting at least one of the at least one agent depots to the body.

9. The method of claim 8, wherein endovascular implantable body is entirely or partially coated with one or more auxiliary agents before connection to the at least one agent depot, the auxiliary agents being implemented such that the auxiliary agents reinforce the mechanical connection of the at least one agent depot to the endovascular implantable body.

10. The method of claim 8, wherein one of the at least one agent depots is provided in sleeve form, the sleeve form having an axis, and corresponds to the length of either a web or a strut of the endovascular implantable body, is slotted along the axis, and represents a clip which is mechanically connected to either the web or the strut of the stent in method step c) using either force action or adhesive.

11. The method of claim 8, wherein the at least one agent depot is implemented in film form and is connected to at least a portion of the face of the abluminal surface of the endovascular implantable body and/or the film formed thereby is additionally provided as perforated corresponding to the geometry of the abluminal surface of the stent, the film material corresponding to areas of the material of the endovascular implantable body being rolled on the film with its abluminal surface being mechanically connected thereto using force action and/or adhesive.

12. The method of claim 8, wherein one of the at least one agent depots represents a preform of a hollow body in sleeve form which is produced using either a hollow body blowing method or an injection-molding method, and wherein the preform represents a negative point of either a stent, web or strut, and the preform is either glued, clicked together, or welded together in step c) on the endovascular implantable body and is mechanically connected to the endovascular implantable body.

13. The method of claim 12, wherein the preform is slotted along the axis, said preform representing a clip which is mechanically connected in step c) to the endovascular implantable body using either force action or adhesive, and further comprising the step of processing the preform so that said preform is cut to the length of either a web or a strut of the endovascular implantable body, is either already slotted or is slotted along the axis in a further step, and said preform represents a clip which is mechanically connected in step c) to either the web or the strut of the endovascular implantable body using either force action or adhesive.

14. A method for producing an agent-charged, endovascular implantable body for prophylaxis or treatment of a stenosis, an aneurysm, or a tumor tissue in a human or animal body, the method comprising: producing at least one agent depots by providing one or more polymers, providing one or more agents, and producing at least one agent depot from the polymers and the agents, the at least one agent depot being implemented in such a manner that the at least one agent depot is mechanically connectable to the surface of the endovascular implantable body using either force action or an adhesive.

* * * * *